United States Patent [19]

Liao et al.

[11] Patent Number: 5,206,312
[45] Date of Patent: Apr. 27, 1993

[54] AROMATIC HYDROXYL-CONTAINING COMPOUNDS CONTAINING ORGANOSILOXANE MOIETIES, EPOXY COMPOUNDS AND CURED PRODUCTS THEREOF

[75] Inventors: Zeng K. Liao, Lake Jackson, Tex.; Chun S. Wang, Tainan, Taiwan

[73] Assignee: The Dow Chemical Company, Midland, Mich.

[21] Appl. No.: 729,508

[22] Filed: Jul. 12, 1991

Related U.S. Application Data

[63] Continuation-in-part of Ser. No. 439,208, Nov. 20, 1989, abandoned.

[51] Int. Cl.$^5$ ............................................ C08F 283/12
[52] U.S. Cl. ................................ 525/474; 525/476; 528/25; 528/27; 528/28; 528/30; 528/33; 528/38; 528/15; 528/43
[58] Field of Search ................ 525/474, 476; 528/25, 528/27, 30, 33, 38, 15, 43

[56] References Cited

U.S. PATENT DOCUMENTS

| | | | |
|---|---|---|---|
| 3,787,452 | 2/1974 | Leumann et al. | 260/348 SC |
| 3,825,618 | 7/1974 | Pepe | 528/25 |
| 3,867,322 | 2/1975 | Leumann et al. | 260/18.5 |
| 3,926,885 | 12/1975 | Keil | 260/29.15 B |
| 4,022,753 | 5/1977 | Lohse et al. | 260/46.5 R |
| 4,276,252 | 6/1981 | Kreis et al. | 528/15 |
| 4,283,513 | 4/1981 | Mikami | 525/476 |
| 4,398,010 | 8/1983 | Adkins | 528/15 |
| 4,555,559 | 11/1985 | Kimura et al. | 528/16 |
| 4,588,800 | 5/1986 | Palensky et al. | 528/15 |
| 4,604,435 | 8/1986 | Koshii et al. | 525/476 |
| 4,707,529 | 11/1987 | Hoffman et al. | 525/476 |
| 4,720,515 | 1/1988 | Iji et al. | 525/476 |
| 4,822,716 | 4/1989 | Onishi et al. | 430/192 |
| 4,877,822 | 10/1989 | Itoh et al. | 523/433 |
| 4,952,643 | 8/1990 | Hiiose et al. | 525/476 |
| 4,954,580 | 9/1990 | Zahir | 525/476 |
| 4,980,427 | 12/1990 | Ryang | 528/27 |

FOREIGN PATENT DOCUMENTS

263237 4/1988 European Pat. Off.

OTHER PUBLICATIONS

"Siloxane Modifiers for Epoxy Resins" Chapter 10, Advances in Chemistry Series 208 Rubber Modified Thermoset Resins, American Chemical Society, 1984.
"Rubber-Modified, Flame-Retardant, High Glass Transition Temperature Epoxy Resins" Chapter 17, Advances in Chemistry Series 208 Rubber Modified Thermoset Resins, American Chemical Society, 1984.
"Impact Properties of Rubber-Modified Epoxy Resin—Graphite-Fiber Compositions", Chapter 20, Advances in Chemistry Series 208 Rubber Modified Thermoset Resins, American Chemical Society, 1984.

*Primary Examiner*—John C. Bleutge
*Assistant Examiner*—M. W. Glass

[57] ABSTRACT

Compounds are prepared which contain both an organosiloxane moiety and either a phenolic hydroxyl group or an epoxide group. Also disclosed are curable and cured compositions.

25 Claims, No Drawings

AROMATIC HYDROXYL-CONTAINING COMPOUNDS CONTAINING ORGANOSILOXANE MOIETIES, EPOXY COMPOUNDS AND CURED PRODUCTS THEREOF

CROSS-REFERENCE TO RELATED APPLICATION

This application is a continuation-in-part of application Ser. No. 07/439,208 filed Nov. 20, 1989, now abandoned.

FIELD OF THE INVENTION

The present invention pertains to aromatic hydroxyl-containing compounds with organosiloxane moieties and epoxy resins prepared therefrom and to cured products thereof.

BACKGROUND OF THE INVENTION

Aromatic hydroxyl-containing compounds have previously been employed to prepare high molecular weight advanced epoxy resins or to cure epoxy compounds; employed in the preparation of epoxy resins and the like. While the resultant products possess good properties, it is always desirable to have available products with improved properties. The aromatic hydroxyl-containing compounds containing organosiloxane moieties of the present invention make it possible to prepare epoxy resins which when cured possess an improvement in one or more of the desirable properties such as thermal stability, moisture resistance, electrical properties and low stress. Therefore, the present invention incorporates the organosiloxane moiety into the aromatic hydroxyl-containing skeleton in an attempt to modify these thermosetting resins. This invention discloses the preparation of novel aromatic hydroxyl containing compounds with an aliphatic or cycloaliphatic organosiloxane moiety in the backbone (skeleton) by the hydrosilylation method, their derivatives and the cured resins which are useful for electronic, coatings and composite applications.

SUMMARY OF THE INVENTION

One aspect of the present invention pertains to compounds having an average of more than one aromatic hydroxyl group and at least one organosiloxane moiety

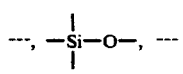

per molecule, said compound being represented by the following general formula I $$Z-(X''-Ar-(OH)_{n^1})_{n^2} \quad (I)$$

wherein Ar is any divalent or multivalent aromatic group or divalent or multivalent inert substituted aromatic group; each X'' is independently a divalent aliphatic or a divalent cycloaliphatic group or a divalent alkoxy or a divalent cycloalkoxy group having from 2 to about 12 carbon atoms; Z is an $n^2$-valent moiety containing at least one organosiloxane moiety; $n^1$ has a value from 1 to about 3; and $n^2$ has a value from 1 to about 200; with the proviso that (a) when $n^2$ has a value of 1, $n^1$ has a value greater than 1; and (b) the —X''—Ar—(OH)$_{n^1}$group(s) is (are) attached to a silicon atom.

Another aspect of the present invention pertains to compounds having an average of more than one vicinal epoxy group and at least one organosiloxane moiety per molecule, said compound being represented by the following general formula II

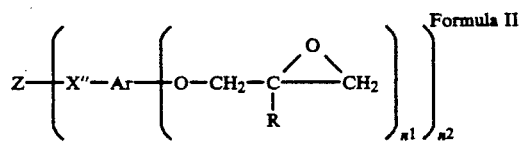

wherein Ar is any aromatic moiety or inert substituted aromatic moiety; each R is independently hydrogen or an alkyl group having from 1 to about 3 carbon atoms; each X'' is independently a divalent aliphatic or a divalent cycloaliphatic group or a divalent alkoxy or or a divalent cycloalkoxy group having from 2 to about 12 carbon atoms; Z is an $n^2$-valent entity containing at least one organosiloxane moiety; $n^1$ has a value from 1 to about 3; and $n^2$ has a value from 1 to about 200, preferably from 1 to about 50, more preferably from 1 to about 20; with the proviso that (a) when $n^2$ has a value of 1, $n^1$ has a value greater than 1; and (b) the group(s)

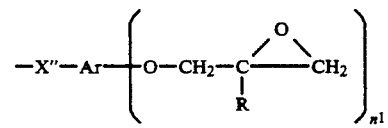

is (are) attached to a silicon atom.

Another aspect of the present invention pertains to an advanced resin prepared by reacting (1) at least one compound containing an average of more than one aromatic hydroxyl group per molecule; and (2) at least one compound containing an average of more than one vicinal epoxy group per molecule; with the proviso that at least one compound of components (1) or (2) is a compound which contains at least one organosiloxane moiety and which compound is represented by general formulas I or II.

Another aspect of the present invention pertains to a curable composition comprising (A) at least one curing agent for component (B), which curing agent is free of aromatic hydroxyl groups and (B) at least one compound having an average of more than one vicinal epoxy group and at least one organosiloxane moiety per molecule.

Another aspect of the present invention pertains to a curable composition comprising (A) at least one compound having an average of more than one vicinal epoxy groups per molecule and (B) at least one compound having an average of more than one aromatic hydroxyl group per molecule; with the proviso that at least one compound of components (A) and (B) is a compound which contains at least one organosiloxane moiety.

Another aspect of the present invention pertains to the product resulting from curing any of the aforementioned curable compositions.

The present invention may suitably comprise, consist of, or consist essentially of, the aforementioned components and compounds.

The invention illustratively disclosed herein suitably may be practiced in the absence of any component which is not specifically disclosed or enumerated herein and nay of the compounds may contain or be free of any substituent not specifically named herein.

DETAILED DESCRIPTION OF THE INVENTION

For purposes of the present invention, the term "aromatic" includes not only the pure aromatic ring compounds containing only carbon atoms in the ring structure, but also the heterocyclic rings containing carbon and sulfur, oxygen or nitrogen atoms in the ring structure.

The term "advanced" as employed herein means the substantially uncured, substantially uncrosslinked, product resulting from reacting a compound having from about two vicinal epoxide groups per molecule with a compound having about two reactive hydrogen groups per molecule.

The compounds containing aromatic hydroxyl groups and organosiloxane moieties which are represented by general formula I can be prepared by the hydrosilylation method which comprises reacting in the presence of a suitable catalyst, with or without a solvent, an aromatic hydroxyl-containing compound containing aliphatic or cycloaliphatic double bonds with an organosiloxane compound as described by John L. Speier in Advances in Organometallic Chemistry, vol. 17, Academic Press, Inc., pp. 407–447, 1979 which is incorporated herein by reference in its entirety. The reaction is usually conducted at temperatures of from about 10° C. to about 150° C., preferably from about 30° C. to about 120° C., more preferably from about 40° C. to about 100° C. Finally, the excessive unreacted ≡Si—H bonds are terminated, quenched, by addition of a mono- or di-unsaturated aliphatic or cycloaliphatic alkene having from about 4 to about 20, preferably from about 6 to about 16, more preferably from about 7 to about 12, carbon atoms such as, for example, noborylene, n-octene, cyclohexene, dicyclopentadiene, styrene, or any combination thereof and the like.

Suitable aromatic hydroxyl-containing compounds which can be employed in this method to prepare the compounds of the present invention include any compound containing at least one aromatic hydroxyl group per molecule and at least one aliphatic or cycloaliphatic double bond. Such compounds include, but are not limited to those compounds represented by the following general formulas III, IV, V, VI, VII, VIII or IX

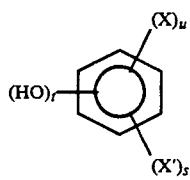

Formula III

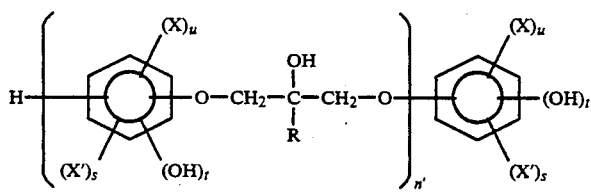

Formula IV

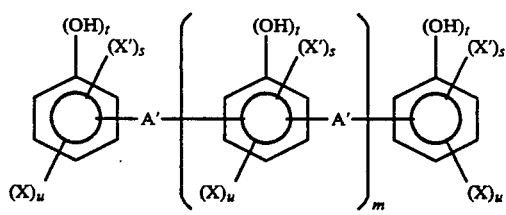

Formula V

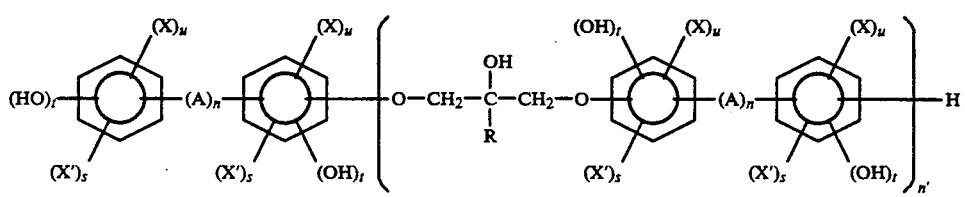

Formula VI

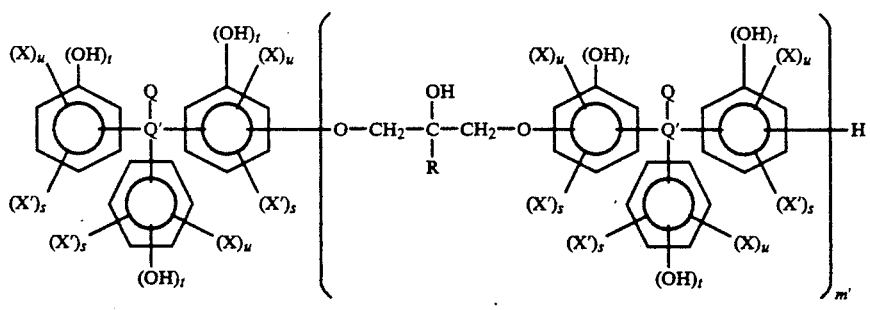

Formula VII

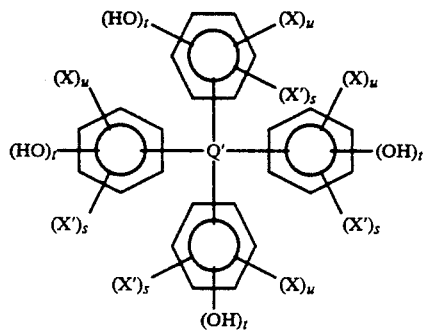

Formula VIII

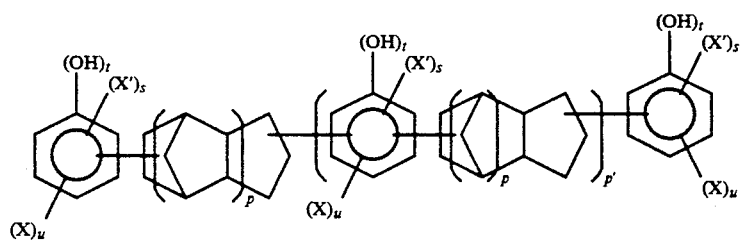

Formula IX wherein each A is independently a divalent hydrocarbyl group having suitably from 1 to about 20, more suitably from 1 to about 15, most suitably from 1 to about 10, carbon atoms, —O—, —S—, —S—S—, —SO—, —SO$_2$—, or —CO—; each A' is independently a divalent hydrocarbyl group having from 1 to about 20, more suitably from 1 to about 10, most suitably from 1 to about 2, carbon atoms; each Q is independently hydrogen or an alkyl group having from 1 to about 10 carbon atoms; each Q' is independently a tetravalent hydrocarbyl group having suitably from 1 to about 20, more suitably from 1 to about 10, most suitably from 1 to about 4, carbon atoms; each R is independently hydrogen or an alkyl group having from 1 to about 3 carbon atoms; each X is independently hydrogen, a hydrocarbyl or hydrocarbyloxy group having suitably from 1 to about 12, more suitably from 1 to about 6, most suitably from 1 to about 4, carbon atoms or a halogen atom, preferably bromine; each X' is independently hydrogen or an unsaturated aliphatic or unsaturated cycloaliphatic group or such unsaturated aliphatic or unsaturated cycloaliphatic group having an oxygen atom between such group and the aromatic ring, and having from 2 to about 12, preferably from 3 to about 9, more preferably from 3 to about 6, carbon atoms such as, for example, —CH$_2$—=CH$_2$, —CH=CH$_2$, —O—CH$_2$— CH=CH$_2$, cyclohexenyl, bicyclo-(2.2.1)hept-1-yl, vinyl benzyl ether or the like with the proviso that at least one of such groups is other than hydrogen; m has an average value suitably from about 0.01 to about 8, more suitably from about 1 to about 6, most suitably from about 2 to about 4; m' suitably has an average value from about zero to about 8, more suitably form about 1 to about 6, most suitably from about 2 to about 4; n has a value of zero or 1; n' suitably has an average value suitably from about 0.001 to about 20, more suitably from about 0.01 to about 12, most suitably from about 0.03 to about 5; each p suitably has a value from zero to about 10, more suitably from about 1 to about 5, most suitably from about 1 to about 3; each p' suitably has an average value from zero to about 8, more suitably from about 1 to about 6, most suitably from about 2 to about 4; and each s, u and t independently has a value from 1 to about 3 with the proviso that the sum of s, u and t satisfies the valency of the ring.

The term hydrocarbyl as employed herein means any aliphatic, cycloaliphatic, aromatic, aryl substituted aliphatic or cycloaliphatic, or aliphatic or cycloaliphatic substituted aromatic groups. The aliphatic groups can be saturated or unsaturated. Likewise, the term hydrocarbyloxy means a hydrocarbyl group having an oxygen linkage between it and the carbon atom to which it is attached.

Particularly suitable phenolic hydroxyl-containing compounds include, for example, 2-allylphenol; 3,3'-diallylbisphenol-A; 3-monoallylbisphenol-A; 4-monoallylether bisphenol-A; cyclohex-1-ylmethylene diphenol or bicyclo-(2.2.1)-hept-1-yl methylene diphenol; 3,3'-diallyl-4,4'- dihydroxydiphenol; 3,3'-diallyl-4,4'-dihydroxyphenyl methane; 4-allyl-2-methoxyphenol; also included are mono- or di-allyl ether of o-cresol-formaldehyde novolac; or phenol-formaldehyde novolac; or any combination thereof and the like.

Suitable hydrosiloxane compounds which can be employed to prepare the compounds containing aromatic hydroxyl groups and organosiloxane moieties include, for example, those represented by the following formulas X, XI, XII, or XIII

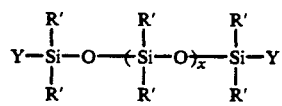  Formula X

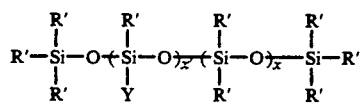  Formula XI

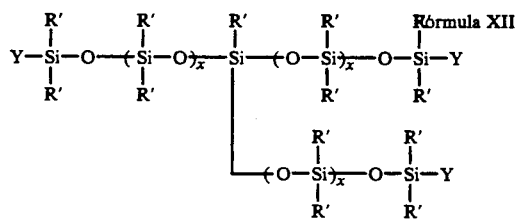  Formula XII

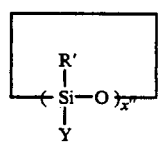  Formula XIII wherein each R' is independently a hydrocarbyl group having suitably from 1 to about 20, more suitably from 1 to about 10, most suitably from 1 to about 4, carbon atoms; each Y is hydrogen; each x independently has a value suitably from zero to about 500, more suitably from zero to about 250, most suitably from zero to about 125; each x' independently has a value suitably from 2 to about 500, more suitably from 2 to about 250, most suitably from 2 to about 125; x" has a value suitably from 3 to about 50, more suitably from about 3 to about 25, most suitably from about 3 to about 20; and the sum of x and x' is suitably from about 2 to about 1000, more suitably from about 2 to about 500, most suitably from about 2 to about 250.

Particularly suitably organohydrosiloxane compounds which can be employed include, for example, 1,1,3,3-tetramethyldisiloxane; 1,1,3,3,5,5-hexamethyltrisiloxane; 1,1,3,3,5,5,7,7-octamethyltetrasiloxane; 1,3-diphenyl-1,3-dimethyldisiloxane; 1,1,3,3-tetraisopropyldisiloxane; 1,3-diphenyl-1,1,3,3-tetrakis-(dimethylsiloxyl)disiloxane; 1,3,5-trimethylcyclotrisiloxane; 1,3,5,7-tetramethylcyclotetrasiloxane; 1,3,5,7,9-pentamethylcyclopentasiloxane; 1,3,5,7,9,11-hexamethylcyclohexasiloxane; 1,3,5,7,9,11,13-heptamethylcycloheptasiloxane; 1,3,5,7,9,11,13,15-octamethylcyclooctasiloxane; 1,1,3,3-tetrakis(trimethylsiloxyl)-disiloxane; polymethylhydrosiloxane(M.W.=300–50,000); methylhydrodimethylsiloxane copolymer(M.W.=120–100,000); dimethylsiloxylterminated-methylhydrophenylmethylsiloxane copolymer (M.W.=120–100,000); combinations thereof and the like.

Suitable solvents or reaction medium which can be employed herein include, for example, aliphatic, cycloaliphatic or aromatic hydrocarbons such as, for example, n-hexane, cyclohexane, octane, toluene, xylene, any combination thereof and the like.

Suitable hydrosilylation catalysts which can be employed include the homogeneous catalysts which are disclosed by John L. Speier in *Advanced In Organometallic Chemistry*, Vol. 17, 407–447, by Academic Press Inc. (1979) which is incorporated herein by reference. Particularly suitable catalysts include, for example, chloroplatinic acid ($H_2PtCl_6$), as well as (($C_2H_4$)$PtCl_2$)$_2$, (bis-(triphenylphosphine)cobalt chloroiridium) ($IrClCo(PPh_3)_2$), dicobalt octacarbonyl ($Co_2(CO)_8$). Also, 10% Pd/C or 5% Pt/C and Raney Ni are effective catalysts for this reaction. Hydrosilylation catalysts which can be used also include those disclosed in U.S. Pat. Nos. 3,775,442, 3,159,601, 3,220,972, all of which are incorporated herein by reference. An effective amount of a platinum catalyst is from about 0.0005 to 1.05 percent by weight of platinum based on the weight of the hydrosilylation mixture.

A second method for preparing the compound containing aromatic hydroxyl groups and also containing organosiloxane moieties is by reacting an aromatic hydroxyl-containing compound having one or more aromatic or heterocyclic rings and at least one ortho or para position relative to an aromatic hydroxyl group available for ring alkylation with a di- or multi-unsaturated aliphatic or cycloaliphatic hydrocarbon containing an organosiloxane moiety in its backbone in the presence of a catalyst and in the presence or absence of a solvent or inert reaction medium such as, for example chlorobenzene. This method is described by Donald L. Nelson in U.S. Pat. No. 4,390,680 and by Paul G. Schrader in U.S. Pat. No. 4,394,496, both of which are incorporated herein by reference in their entirety. Particularly suitable catalysts include, for example, Lewis acids such as, for example, HCl, $H_2SO_4$, $BF_3$.etherate, $TiCl_4$, $ZrCl_4$, $CH_3SO_3H$, p-toluene sulfonic acid, oxalic acid, combinations thereof and the like.

Suitable aromatic hydroxyl-containing compounds which can be employed to prepare the compounds containing aromatic hydroxyl groups and also containing organosiloxane moieties by this second method include the previously mentioned compounds represented by formulas III, IV, V, VI, VII, VIII or IX except that each X' is independently hydrogen, a hydrocarbyl or hydrocarbyloxy group having suitably from 1 to about 12, more suitably from 1 to about 6, most suitably from 1 to about 4, carbon atoms or a halogen atom, preferably bromine. Also suitable are the heterocyclic compounds containing an aromatic hydroxyl group such as, for example, those represented by the following general formulas XIV, XV, XVI or XVII

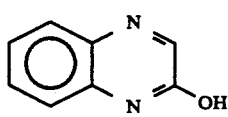  Formula XIV

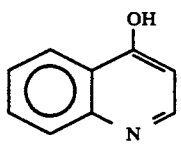  Formula XV

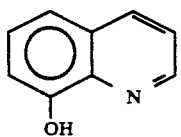
Formula XVI

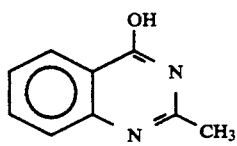
Formula XVII

These heterocyclic ring compounds can, if desired contain inert ring substituents such as, for example, aliphatic or aromatic hydrocarbon groups containing suitably from 1 to about 20, more suitably from 1 to about 15, most suitably from 1 to about 10 carbon atoms, or a halogen, preferably bromine.

Suitable di- or multi-unsaturated aliphatic or cycloaliphatic compounds containing organosiloxane moieties in their backbone include, for example, those represented by the following general formulas XVIII, XIX, XX or XXI

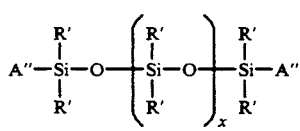
Formula XVIII

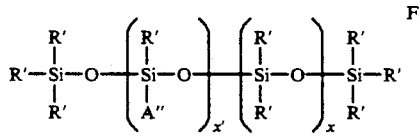
Formula XIX

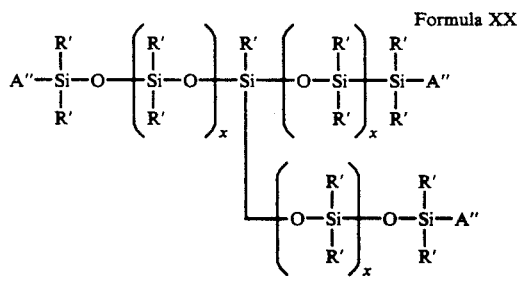
Formula XX

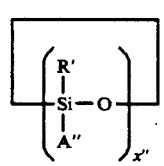
Formula XXI wherein each R', x, x' and x" is as previously defined in Formulas X–XIII; and each A" is an unsaturated aliphatic or unsaturated cycloaliphatic group containing suitably from 1 to about 20, more suitably from 1 to about 15, most suitably from 1 to about 10, carbon atoms. Particularly suitable A" groups include, for example,

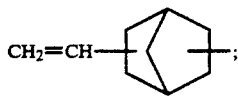

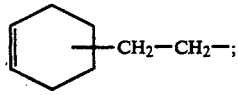

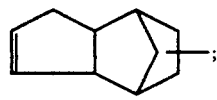

or the like.

These di- or multi-unsaturated aliphatic or di-or multi-unsaturated cycloaliphatic compounds containing organosiloxane moieties in their backbone can be prepared via hydrosilylation of corresponding unsaturated aliphatic or cycloaliphatic alkenes with corresponding hydrosiloxane compounds represented by formulas X, XI, XII or XIII as described above.

Suitable di- or multi-unsaturated aliphatic or di- or multi-unsaturated cycloaliphatic compounds used for making the compounds represented by formulas XVIII to XXI include, for example, those having from about 4 to about 400, preferably from about 4 to about 200 carbon atoms, such as, for example, 1,4-pentadiene, 1,4-hexadiene, 1,5-hexadiene, 1,7-octadiene, 4-methyl-1,3-pentadiene, 5-vinyl-2-norbornene; 4-vinyl-1-cyclohexene; dicyclopentadiene; 1,4-cyclohexadiene; cyclopentadiene; bicyclo-(2.2.1)-hepta-2,5-diene; pentacyclo-(8.2.1.1$^{4,7}$.0$^{2,9}$.0$^{3,8}$)-tetradeca-5,11-diene; methylcyclopentadiene dimer; 5-ethylidene-2-norbornene; 5-methylene-2-norbornene; (−) limonene; (+) limonene; 1,5-cyclodecadiene; 1,5-cyclooctadiene; and the like.

The novel compounds of the present invention which contain aromatic hydroxyl groups and which also contain organosiloxane moieties include those compounds represented by the following general formula I $$Z-(X''-Ar-(OH)_{n1})_{n2} \qquad (I)$$

wherein Ar is any divalent or multivalent aromatic group or divalent or multivalent inert substituted aromatic group; each X" is independently a divalent aliphatic or a divalent cycloaliphatic group or a divalent alkoxy or a divalent cycloalkoxy group having from 2 to about 12, preferably from about 3 to about 9, more preferably from about 3 to about 6 carbon atoms; Z is an $n^2$-valent group containing at least one organosiloxane moiety; $n^1$ has a value from 1 to about 3, preferably from 1 to about 2; and $n^2$ has a value from 1 to about 200, preferably from 1 to about 50, more preferably from 1 to about 20; with the proviso that when $n^2$ has a value of 1, $n^1$ has a value greater than 1.

Preferably, the compounds of the present invention which contain aromatic hydroxyl groups and which also contain organosiloxane moieties include those compounds represented by the aforementioned general formulas X, XI, XII, or XIII wherein each R' is independently a hydrocarbyl group having suitably from 1 to about 20, more suitably from 1 to about 10, most suitably from 1 to about 4, carbon atoms; each Y is a hydrocarbyl group having from 2 to about 20 carbon atoms or an entity represented by the following formulas XXII, XXIII, XXIV, XXV, XXVI, XXVII, or XXVIII with the proviso that at least an average of more than one Y is other than a hydrocarbyl group:

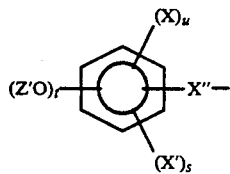

Formula XXII

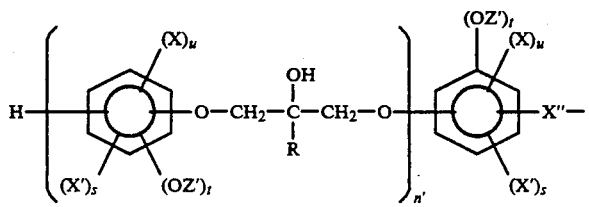

Formula XXIII

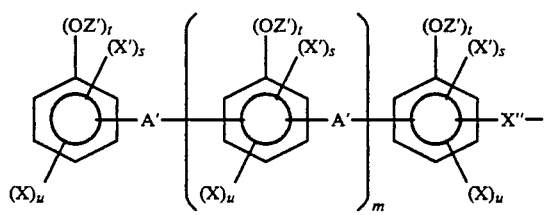

Formula XXIV

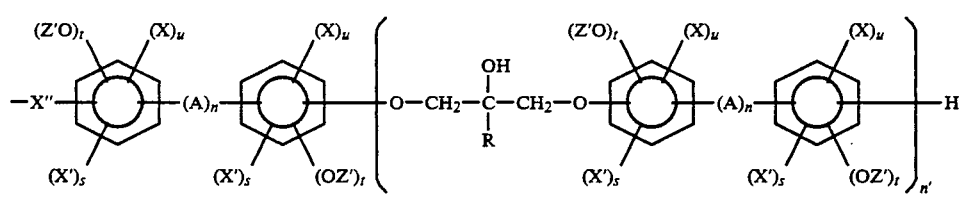

Formula XXV

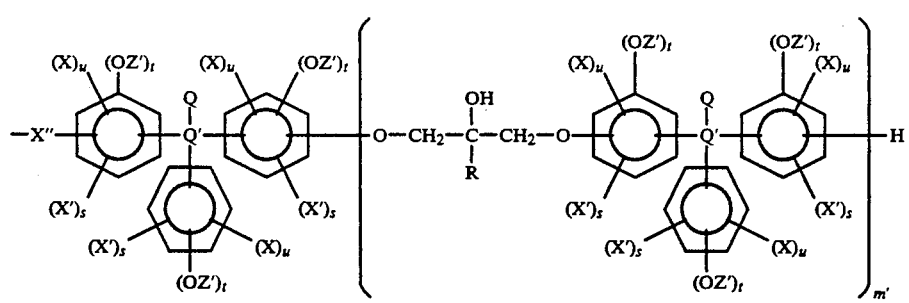

Formula XXVI

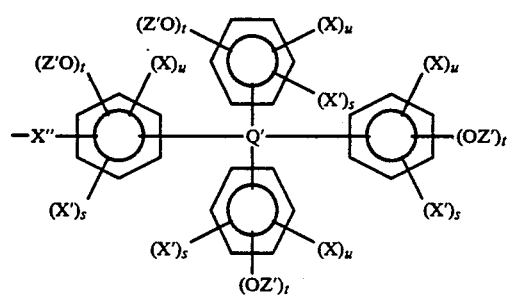

Formula XXVII

-continued

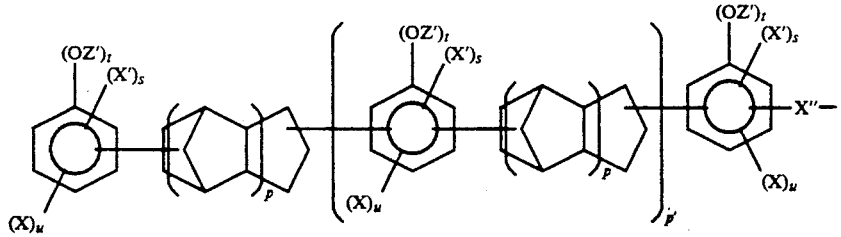

Formula XXVIII each A is independently a divalent hydrocarbyl group having from 1 to about 20 carbon atoms; —O—, —S—, —S—S—, —SO—, —SO$_2$—, or —CO—; each A' is independently a divalent hydrocarbyl group having from 1 to about 20 carbon atoms; each Q is independently hydrogen or an alkyl group having from 1 to about 10 carbon atoms; each Q' is independently a tetravalent hydrocarbyl group having from 1 to about 20 carbon atoms; each R is independently hydrogen or an alkyl group having from 1 to about 3 carbon atoms; each X is independently hydrogen, a hydrocarbyl or hydrocarbyloxy group having from 1 to about 12 carbon atoms, a halogen atom; each X' is independently hydrogen or a monovalent aliphatic or a monovalent cycloaliphatic group; each X" is independently a divalent aliphatic or a divalent cycloaliphatic group or a divalent alkoxy or or a divalent cycloalkoxy group having from 2 to about 12, preferably from about 3 to about 9, more preferably from about 3 to about 6 carbon atoms; each Z' is hydrogen; each m independently has an average value from about 0.01 to about 8; each m' independently has an average value from about zero to about 8; each n independently has a value of zero or 1; each n' independently has an average value from about 0.001 to about 20; each n$^1$ independently has a value from 1 to about 3; each p independently has a value from zero to about 10; each p' independently has an average value from zero to about 8; and each s, t and u independently has a value from 1 to about 3 with the proviso that the sum of s, t and u satisfies the valency of the ring; each x independently has a value from zero to about 500, preferably from zero to about 250, more preferably from zero to about 125; each x' independently has a value from 2 to about 500, preferably from 2 to about 250, more preferably from 2 to about 125; each x" independently has a value from 3 to about 50, preferably from 3 to about 40, more preferably from 3 to about 15; and the sum of x and x' is from about 2 to about 1000.

The epoxy-containing compounds represented by General Formula II of the present invention can be prepared by reacting the aromatic hydroxy-containing compounds represented by General Formula I with an epihalohydrin and dehydrohalogenating the resultant product with a basic acting compound such as, for example, sodium hydroxide, potassium hydroxide, lithium hydroxide, sodium carbonate, potassium carbonate, combinations thereof and the like. Methods for the preparation of epoxy-containing compounds from compounds containing aromatic hydroxyl groups is more fully described by Wang et al. in U.S. Pat. No. 4,499,255 and U.S. Pat. No. 4,778,863 which are incorporated herein by reference in their entirety.

Preferably, the epoxy-containing compounds of the present invention which also contain organosiloxane moieties include those compounds represented by the aforementioned general formulas X, XI, XII, or XIII wherein each R' is independently a hydrocarbyl group having suitably from 1 to about 20, more suitably from 1 to about 10, most suitably from 1 to about 4, carbon atoms; each Y is a hydrocarbyl group having from 2 to about 20 carbon atoms or an entity represented by the following formulas XXII, XXIII, XXIV, XXV, XXVI, XXVII, or XXVIII with the proviso that at least an average of more than one Y is other than a hydrocarbyl group:

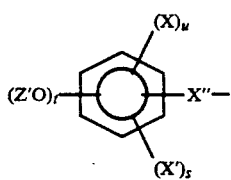

Formula XXII

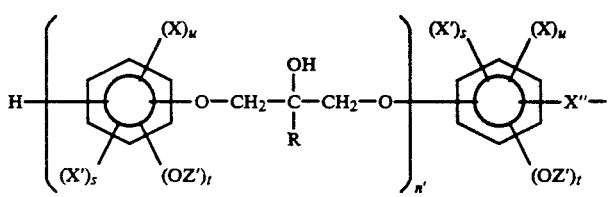

Formula XXIII

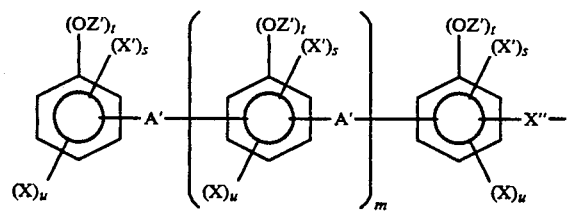

Formula XXIV

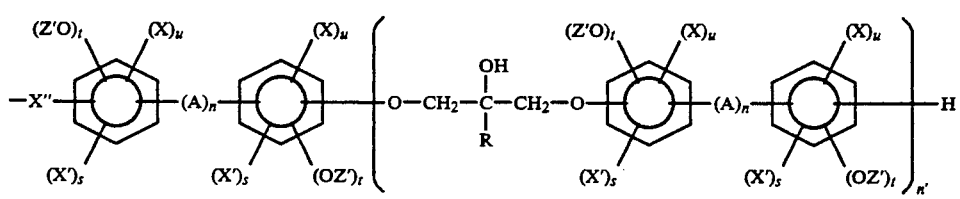

Formula XXV

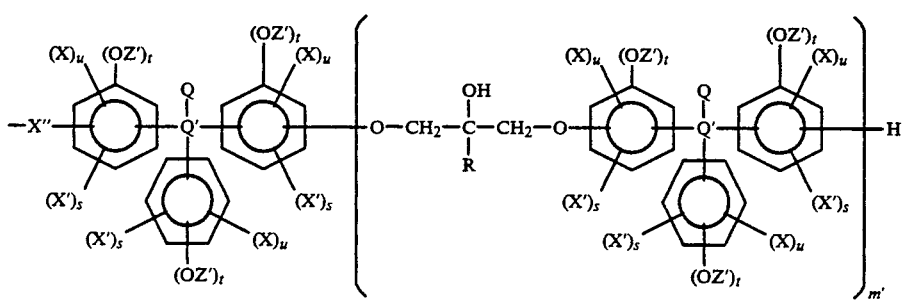

Formula XXVI

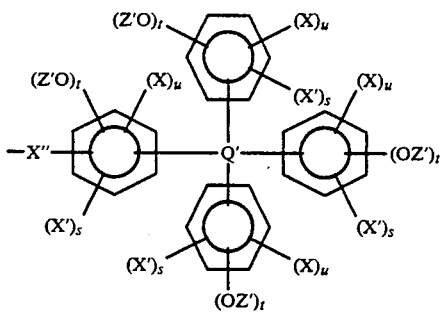

Formula XXVII

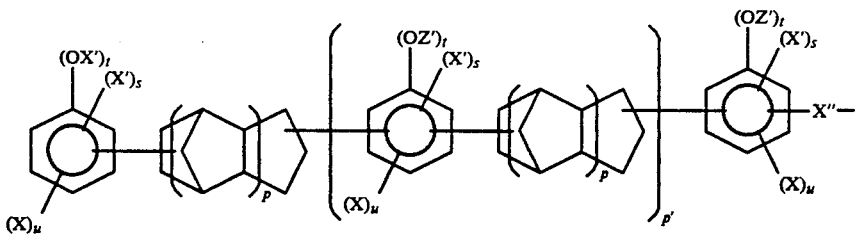

Formula XXVIII each A is independently a divalent hydrocarbyl group having from 1 to about 20 carbon atoms, —O—, —S—, —S—S—, —SO—, —SO$_2$—, or —CO—; each A' is independently a divalent hydrocarbyl group having from 1 to about 20 carbon atoms; each Q is independently hydrogen or an alkyl group having from 1 to about 10 carbon atoms; each Q' is independently a tetravalent hydrocarbyl group having from 1 to about 20 carbon atoms; each R is independently hydrogen or an alkyl group having from 1 to about 3 carbon atoms; each X is independently hydrogen, a hydrocarbyl or hydrocarbyloxy group having from 1 to about 12 carbon atoms, a halogen atom; each X' is independently hydrogen or a monovalent aliphatic or a monovalent cycloaliphatic group; each X" is independently a divalent aliphatic or a divalent cycloaliphatic group or a divalent alkoxy or or a divalent cycloalkoxy group having from 2 to about 12, preferably from about 3 to about 9, more preferably from about 3 to about 6 carbon atoms; each Z' is glycidyl group or methyl, ethyl, propyl or butyl substituted glycidyl group; each m independently has an average value from about 0.01 to about 8; each m' independently has an average value from about zero to about 8; each n independently has a value of zero or 1; each n' independently has an average value from about 0.001 to about 20; each n$^1$ independently has a value from 1 to about 3; each p independently has a value from zero to about 10; each p' independently has an average value from zero to about 8; and each s, t and u independently has a value from 1 to about 3 with the proviso that the sum of s, t and u satisfies the valency of the ring; each x independently has a value from zero to about 500, preferably from zero to about 250, more preferably from zero to 125; each x' independently has a value from 2 to about 500, preferably from 2 to about 250, more preferably from 2 to about 125; each x" independently has a value from 3 to about 50, preferably from 3 to about 40, more preferably from 3 to about 15; and the sum of x and x' is from about 2 to about 1000.

The advanced resins of the present invention can be prepared by reacting the desired epoxy-containing compound(s) with the desired aromatic hydroxy-containing compound(s) in the presence of a suitable catalyst and in the absence of presence of one or more suitable solvents.

Suitable aromatic hydroxy-containing compounds with one or more aliphatic or cycloaliphatic siloxane moieties in their backbone which can be employed herein to prepare the advanced resins include, for example, those represented by the aforementioned formula I. These aromatic hydroxy-containing compounds can also be combined with other compounds having an average of about 2 hydrogen atoms per molecule which are reactive with vicinal epoxy groups or when the epoxide-containing component contains an epoxide-containing compound which contains aliphatic or cycloaliphatic siloxane moieties in their backbone (those represented by General Formula II), then these other aromatic hydroxyl-containing compounds can be employed as the sole aromatic hydroxyl-containing constituent. Suitable such phenolic hydroxyl containing compounds include, for example, resorcinol; catechol; hydroquinone; bisphenol-A; bisphenol-F; 9,9'-bisphenol fluorene, bisphenol-K; bisphenol-S; tetramethylbisphenol-A; tetra-t-butylbisphenol-A; 3,3',5,5'-tetrabromobisphenol-A; 3,3',5,5'-tetramethyl-4,4'-dihydroxylbiphenol; 3,3',5,5',-tetramethyl-2,2',6,6'-tetrabromo-4,4'-dihydroxylbiphenol, the reaction product of dicyclopentadiene or oligomers thereof and a phenolic hydroxyl-containing compound, mixtures thereof and the like. Such compounds are disclosed by Berman et al. in U.S. Pat. No. 4,727,119; by Bertram et al. in U.S. Pat. No. 4,594,291 which are incorporated herein by reference.

Suitable epoxy resins which can be employed herein are represented by the following formula II

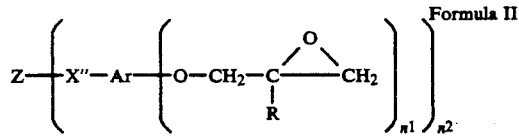

Formula II wherein Ar is any aromatic moiety or inert substituted aromatic moiety; each R is independently hydrogen or an alkyl group having from 1 to about 3 carbon atoms, preferably hydrogen; each X" is independently a divalent aliphatic or a divalent cycloaliphatic group or a divalent alkoxy or or a divalent cycloalkoxy group having from 2 to about 12, preferably from about 3 to about 9, more preferably from about 3 to about 6 carbon atoms; Z is an $n^2$-valent entity containing at least one organosiloxane moiety; $n^1$ has a value from 1 to about 3, preferably 1 to about 2; and $n^2$ has a value from 1 to about 200, preferably from 1 to about 50, more preferably from 1 to about 20; with the proviso that (a) when $n^2$ has a value of 1, $n^1$ has a value greater than 1; and (b) the group(s)

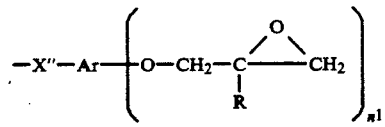

is (are) attached to a silicon atom. These epoxide-containing compounds can also be combined with other epoxide compounds such as glycidyl ethers, glycidyl amines, glycidyl esters and aliphatic or cycloaliphatic epoxides, or when the aromatic hydroxy-containing component which contains aliphatic or cycloaliphatic siloxane moieties in its backbone, then these epoxide-containing compounds can be employed as the sole epoxide-containing constituent. Particularly suitable epoxy resins are the glycidyl ethers of phenols, such as, for example, o-cresol-formaldehyde epoxy novolac, phenol-formaldehyde epoxy novolac, diglycidyl ether of bisphenol A, diglycidyl ether of bisphenol F, diglycidyl ether of bisphenol K, diglycidyl ether of fluorene, triglycidyl ether of 1,1,1-trisphenol methane, hydrocarbon-phenol epoxy resins or hydrocarbon-containing substituted phenol epoxy resins such as glycidyl ethers of cyclopentadiene-phenol resins, glycidyl ethers of dicyclopentadiene-phenol resins, glycidyl ethers of cyclopentadiene-cresol resins, glycidyl ethers of dicyclopentadiene-cresol esins; bisphenol-A, bisphenol-F, bisphenol-K, bisphenol-S, 9,9'-bisphenol fluorene, epoxy resins, any combination thereof and the like. Also suitable are N,N,N',N'-tetraglycidyl methylene dianiline and the like; diglycidyl esters of hexahydrophthalate and the like; cycloaliphatic epoxides such as, for example, 3,4-epoxycyclohexylmethyl, 3',4'-epoxycyclohexane carboxylate, or any combination thereof and the like.

Suitable catalysts which can be employed to prepare the advanced resins, include, for example, tetrahydrocarbylphosphonium compounds, cycloalkyltriphenyl phosphonium compounds, methylenebis(triphenylphosphonium) compounds, or any combination thereof and the like; wherein the anion portion of such compounds are carboxylates, carboxylate-carboxylic acid complexes, halides, phosphates, bicarbonates, formates, acetates, bisphosphate, phenates, bisphenates, tetrafluoborates, or any combination thereof and the like. Particularly suitable catalysts include, for example, ethyltriphenylphosphonium acetate.acetic acid complex, ethyltriphenylphosphonium bromide, ethyltriphenylphosphonium chloride, ethyltriphenylphosphonium iodide, ethyltriphenylphosphonium phosphate, ethyltriphenylphosphonium tetrafluoborate, tetrabutylphosphonium acetate.acetic acid complex, tetrabutylphosphonium bromide, tetrabutylphosphonium chloride, tetrabutylphosphonium iodide, tetrabutylphosphonium phosphate, tetrabutylphosphonium tetrafluoborate, cyclopropyltriphenylphosphonium acetate.acetic acid complex, cyclobutyltriphenylphosphonium acetate.acetic acid complex, cyclopentyltriphenylphosphonium acetate.acetic acid complex, cyclohexyltriphenylphosphonium acetate.acetic acid complex, cyclopropyltriphenylphosphonium acetate.a- cetic acid complex, cyclobutyltriphenylphosphonium acetate.acetic acid complex, cyclopentyltriphenylphosphonium acetate.acetic acid complex, cyclohexyltriphenylphosphonium acetate.acetic acid complex, cyclopropyltriphenylphosphonium formate, cyclobutyltriphenylphosphonium formate, cyclopentyltriphenylphosphonium formate, cyclohexyltriphenylphosphonium formate, cyclopropyltriphenylphosphonium formate, cyclobutyltriphenylphosphonium formate, cyclopentyltriphenylphosphonium formate, cyclohexyltriphenylphosphonium formate, cyclobutyltriphenylphosphonium bromide, cyclopentyltriphenylphosphonium bromide, cyclohexyltriphenylphosphonium bromide, cyclopropyltriphenylphosphonium bromide, cyclobutyltriphenylphosphonium bromide, cyclopentyltriphenylphosphonium bromide, cyclohexyltriphenylphosphonium bromide, cyclobutyltriphenylphosphonium chloride, cyclopentyltriphenylphosphonium chloride, cyclohexyltriphenylphosphonium chloride, cyclopropyltriphenylphosphonium chloride, cyclobutyltriphenylphosphonium chloride, cyclopentyltriphenylphosphonium chloride, cyclohexyltriphenylphosphonium chloride, cyclobutyltriphenylphosphonium iodide, cyclopentyltriphenylphosphonium iodide, cyclohexyltriphenylphosphonium iodide, cyclopropyltriphenylphosphonium iodide, cyclobutyltriphenylphosphonium iodide, cyclopentyltriphenylphosphonium iodide, cyclohexyltriphenylphosphonium iodide, cyclobutyltriphenylphosphonium tetrafluoborate, cyclopentyltriphenylphosphonium tetrafluoborate, cyclohexyltriphenylphosphonium tetrafluoborate, cyclopropyltriphenylphosphonium tetrafluoborate, cyclobutyltriphenylphosphonium tetrafluoborate, cyclopentyltriphenylphosphonium tetrafluoborate, cyclohexyltriphenylphosphonium tetrafluoborate, any combination thereof and the like.

The epoxy-containing compound and the aromatic hydroxy-containing compound are employed in any suitable amount so as to produce the particular advanced resin desired. If it is desired to prepare an advanced product that is terminated by epoxy groups, the epoxy-containing component is employed in excess; whereas if it is desired for the advanced product to be terminated in phenolic hydroxy groups, the phenolic hydroxyl-containing component is employed in excess. If very high molecular weight advanced products is desired, the ratio of phenolic hydroxyl groups to epoxy groups approaches 1:1 with the highest molecular weight products being obtained when the ratio is 1:1. Most generally, the compounds are employed in ratios which provide an aromatic hydroxyl group to epoxide group ratio of from about 0.005:1 to about 20:1, preferably from about 0.05:1 to about 15:1, more preferably from about 0.5:1 to about 5:1.

Suitable solvents of inert reaction medium which can be employed in the preparation of the advanced resins of the present invention include, for example, aromatic hydrocarbons, alcohols, glycol ethers, ketones, combinations thereof and the like. Particularly suitable such solvents include, for example, benzene, toluene, xylene, methanol, ethanol, n-propanol, i-propanol, t-butanol, sec-butanol, acetone, methyl ethyl ketone, methyl isobutyl ketone, diethylene glycol dimethyl ether, dipropylene glycol dimethyl ether, combinations thereof and the like.

Suitable curing agents which can be employed in the curable compositions of the present invention include, for example, those compounds containing a plurality of primary or secondary aliphatic, cycloaliphatic or aromatic amine groups, amides, di- and polycarboxylic acids or anhydrides thereof, guanidines, biguanides, urea-aldehyde resins, melamine-aldehyde resins, alkoxylated urea-aldehyde resins, alkoxylated melamine-aldehyde resins, phenol-aldehyde resins, halogen or alkyl substituted phenol-aldehyde resins, Lewis acids, combinations thereof and the like. Particularly suitable curing agents include, for example, dicyandiamide, hexamethylenediamine, N,N-diethylpropylenediamine, 1,2-diaminocyclohexane, bis-(4-aminocyclohexyl)-methane, 3,5,5-trimethyl-3-(aminomethyl)cyclohexylamine ("isophoronediamine"), 2,4,6-tri-(dimethylaminomethyl)-phenol, p-phenylenediamine, 4,4'-diaminodiphenylsulfone, or bis-(4-aminophenyl)-methane; or polyamides formed from aliphatic polyamines and dimerized or trimerized unsaturated fatty acids, resorcinol, catechol, hydroquinone,2,2-bis-(4-hydroxyphenyl)-propane (bisphenol A), 3,3',5,5'-tetrabromo bisphenol A, bisphenol F, bisphenol K, bisphenol S, phenol/formaldehyde novolac resins, cresol/formaldehyde novolac resins; boron trifluoride and its complexes with organic compounds, for example $BF_3$-ether complexes or $BF_3$-amine complexes; hexahydrophthalic anhydride, 5-norbornene-2,3-dicarboxylic anhydride, methyl-5-norbornene-2,3-dicarboxylic anhydride, combinations thereof and the like. Also suitable are the anhydride derivatives or organosiloxane compounds which are disclosed by H. S. Ryang in U.S. Pat. No. 4,381,396, by H. S. Ryang in U.S. Pat. No. 4,511,701, by M. A. Buese in U.S. Pat. No. 4,598,135, and by J. E. Hallgren, et al. in U.S. Pat. No. 4,634,755 all of which are incorporated herein by reference. Particularly suitable such curing agents include, 5,5'-(1,1,3,3-tetramethyl-1,3 -disiloxanediyl)bis-norbornane-2,3-dicarboxylic anhydride, dianhydride terminated polydiorganosiloxanes having a weight average molecular weight of from about 200 to about 100,000, norbornenyl anhydride substituted cyclicorganosiloxane having a weight average molecular weight of from about 500 to about 100,000 and any combination thereof.

If desired, curing accelerators can also be employed in the curing reaction. Examples of suitable such accelerators are tertiary amines or salts or quaternary ammonium compounds thereof, for example benzyldimethylamine, 2,4,6-tris-(dimethylaminomethyl)phenol, 1-methylimidazole, 2-methylimidazole, 2-ethyl-4-methylimidazole, 4-aminopyridine, tripentylammonium phenate or tetramethylammonium chloride; or alkali metal alcoholates, for example sodium alcoholates of 2,4-dihydroxy-3-hydroxymethylpentane, and the like.

The curing agents are employed in an amount which will effectively cure the composition containing the epoxy resin. These amounts will depend upon the particular epoxy resin and curing agent employed; however, suitable amounts include, for example, from about 0.75 to about 1.5, more suitably from about 0.85 to about 1.2, most suitably from about 0.9 to about 1.1 equivalents of curing agent per epoxide equivalent for those curing agents which cure by reacting with the epoxy group of the epoxy resin The *Handbook of Epoxy Resins* by Lee and Neville, McGraw-Hill, 1967, which is incorporated herein by reference, contains various discussions concerning the curing of epoxy resins as well as a compilation of suitable curing agents. Also, *EPOXY RESINS Chemistry and Technology*, 2nd Ed., edited by Clayton A. May, Marcel Dekker, Inc. (1988) which is incorporated herein by reference contains discussion on curing epoxy resins.

The epoxy resins and curable compositions of the present invention can be blended with other materials such as, for example, solvents or diluents, fillers, pigments, dyes, flow modifiers, thickeners, reinforcing agents, surfactants, antioxidants, surfactants, combinations thereof and the like.

These additives are added in functionally equivalent amounts e.g., the pigments and/or dyes are added in quantities which will provide the composition with the desired color.

Solvents or diluents which can be employed herein include, for example, aliphatic and aromatic hydrocarbons, ketones, alcohols, glycol ethers, combinations thereof and the like. Particularly suitable solvents or diluents include, for example, toluene, benzene, xylene, acetone, methyl ethyl ketone, methyl isobutyl ketone, diethylene glycol methyl ether, dipropylene glycol methyl ether, combinations thereof and the like.

Reinforcing materials which can be employed herein include natural and synthetic fibers in the form of woven, mat, monofilament, multifilament, and the like. Suitable reinforcing materials include, glass, ceramics, nylon, rayon, cotton, aramid, graphite, combinations thereof and the like.

Suitable fillers which can be employed herein include, for example, inorganic oxides, ceramic microspheres, plastic microspheres, combinations thereof and the like.

The compositions of the present invention can be employed in such applications as adhesives, coatings, laminates, composites, encapsulants, filament winding, molding, and the like.

The following examples are illustrative of the invention but are not to be construed as to limiting the scope thereof in any manner.

EXAMPLE 1

Preparation of 1,3-bis-(3-(2-hydroxylphenyl)-propyl-1,1,3,3-tetramethyldisiloxane To a 85 ml toluene solution containing 67.1 g (0.5 mole) of 2-allylphenol and 0.4 g of a 5% solution of $H_2PtCl_6$ in t-amyl alcohol is added a solution consisting of 15 ml of toluene and 38.8 g (0.25 mole) of 1,1,3,3-tetramethyldisiloxane at 75° C. The addition is complete in 1 hour. The mixture is heated at 85° C. for 1 hour and then at 105° C. for 3 hours. After washing successively three times with 100 ml portions of water, 101 g of the 2:1 molar adduct, 1,3-bis-(3-(2-hydroxylphenyl)-propyl)-1,1,3,3-tetramethyldisiloxane (>92% pure by gel chromatography, GC) having a light straw color is obtained after stripping off solvent. The structure of the product 1,3-bis-(3-(2-hydroxylphenyl)-propyl)-1,1,3,3-tetramethyldisiloxane is confirmed by 1H NMR and IR (neat).

IR (neat): 3350 (broad, aromatic hydroxyl), 1050–1100 (strong, siloxane) cm$^{-1}$; ≡Si—H bond absorption peak at 2100–2200 cm$^{-1}$ disappeared;

1H NMR (CDCl$_3$-TMS): 0–0.8 ppm (m, Si—CH$_3$ and Si—CH$_2$—), 1.6 ppm (m, —CH$_2$—), 2.7 ppm (t, Ar—CH$_2$—), 5.5–5.6 ppm (broad ArOH, D$_2$O exchangeable), 6.8–7.0 ppm (m, Ar—H).

EXAMPLE 2

Preparation of Aromatic Hydroxyl-Containing Compound with Organodimethyl Siloxane Moiety To a 100 ml toluene solution of 100 g hydromethylsiloxane-dimethylsiloxane copolymer terminated with trimethylsiloxy groups; (15% hydromethylsiloxy content; 5.6 eq. Si—H/mole, M.W. 2250) is added 20 ml of a toluene solution containing 13.14 g (0.098 mole) of 2-allylphenol and 0.16 g of a 5% solution of $H_2PtCl_6$ in t-amyl alcohol at 70° C. for 30 minutes. The mixture is then heated at 80°–85° C. for 4 hrs. 28.25 g (0.3 mole) of norborylene is added in 10 minutes at 65° C. and further reacted at 85° C. for another 8 hrs. The mixture is dissolved in 150 ml methyl ethyl ketone and washed successively four times with 100 ml portions of water, 123 g of viscous liquid (2.2 eq. of aromatic hydroxyl/mole based on charge) is obtained after stripping off solvent and excess of norborylene at 130° C./15 mm Hg. The structure of the product, aromatic hydroxy-containing compound with organodimethyl siloxane moiety, is confirmed by 1H NMR and IR as follows:

IR (neat): 3400 cm$^{-1}$ (broad, aromatic hydroxyl), 1050–1100 cm$^{-1}$ (strong, siloxane); ≡Si—H absorption band at 2100–2200 cm$^{-1}$ disappeared in IR.

1H NMR (CDCl$_3$-TMS): 0.5–0.8 ppm (m, ≡Si—CH$_3$ and ≡Si—CH$_2$—), 1.6–2.4 ppm (m, aliphatic and cycloaliphatic C—H), 3.00 ppm (t, Ar—CH$_2$—), 5.0 ppm (broad, Ar—OH, D$_2$O exchangeable), 7.2 ppm (m, Ar—H).

EXAMPLE 3

Preparation of Aromatic Hydroxyl-Containing Compound with Organodimethyl Siloxane Moiety To a 100 ml toluene solution of 100 g hydromethylsiloxane-dimethylsiloxane copolymer terminated by trimethylsiloxy groups (15% hydromethylsiloxy content, 5.63 eq. ≡Si—H/mole, M.W.=2250) is added 20 ml toluene solution containing 20.13 g (0.15 mole) of 2-allylphenol and 0.25 g of a 5% solution of $H_2PtCl_6$ in t-amyl alcohol at 85° C. for 1hr. The clear solution is then heated at 95° C. for 4 hrs. 22 g (0.196 mole) of octene-1 is then added at this temperature in 10 minutes and heated at 95° C. for 9 hrs. The mixture is dissolved in 150 ml methyl ethyl ketone and the solution is washed successively four times with 100 ml portions of water. The organic layer is collected and 125 g of viscous liquid (3.4 eq. of aromatic hydroxyl/mole) is obtained after stripping off the solvent and excessive octene-1 at 130° C./15 mm Hg. The structure of the product, aromatic hydroxy-containing compound with organodimethyl siloxane moiety, is confirmed by 1H NMR and IR as follows:

IR (neat): 3450 cm$^{-1}$ (broad, aromatic hydroxyl), 1000–1100 cm$^{-1}$ (strong, siloxane). ≡Si—H bond absorption peak at 2100–2200 cm$^{-1}$ disappeared in IR.

1H NMR (CDCl$_3$-TMS): 0.4–0.6 ppm (m, ≡Si—CH$_3$ and ≡Si—CH$_2$—), 1.0–2.4 ppm (m, aliphatic and cycloaliphatic C—H), 3.00 ppm (t, Ar—CH$_2$—), 5.6 ppm (broad, Ar—OH, D$_2$O exchangeable), 7.1–7.5 ppm (m, Ar—H).

EXAMPLE 4

Preparation of Aromatic Hydroxyl-Containing Compounds with Organodimethylsiloxane Moiety To a 100 ml toluene solution of 100 g hydromethylsiloxanedimethylsiloxane copolymer (trimethylsiloxy terminate; 30% hydromethylsiloxy content: 10.25 eq. Si—H/mole; M.W. 2050) is added a 20 ml toluene solution containing 33.54 g of 2-allylphenol (0.25 mole) and 0.25 g 5% $H_2PtCl_6$ in t-amyl alcohol at 85° C. for 20 min. The clear solution is then heated at 90° C. for 4 hrs. 40.1 g of norborylene (0.50 mole) is then added at this temperature in 10 minutes and heated at 85° C. for 8 hrs. The mixture is dissolved in 150 ml methyl ethyl ketone and the solution is washed successively four times with 100 ml portions of $H_2O$. The organic layer is collected and 142 g of viscous liquid (5.0 eq. of aromatic hydroxyl/mole) is obtained after stripping off the solvent and excessive norborylene at 130° C./15 mm Hg. The structure is confirmed by 1H NMR and IR:

IR (neat): 3450 cm$^{-1}$ (broad, aromatic hydroxyl), 1000–1100 cm$^{-1}$ (strong, siloxane). ≡Si—H bond absorption peak at 2100–2200 cm$^{-1}$ disappeared in IR.

1H NMR (CDCl$_3$-TMS): 0.4–0.6 ppm (m, ≡Si—CH$_3$ and ≡Si—CH$_2$—), 1.0–2.4 ppm (m, aliphatic and cycloaliphatic C—H), 3.00 ppm (t, Ar—CH$_2$—), 5.7 ppm (broad, Ar—OH, D$_2$O exchangeable), 7.0–7.5 ppm (m, Ar—H).

EXAMPLE 5

Preparation of Aromatic Hydroxyl-Containing Compound with Organodimethylcyclosiloxane Moiety To a 30 ml toluene solution of 80.46 g (0.49 eq.) 4-allyl-2-methoxypheno(eugenol) and 0.25 g of a 5% $H_2PtCl_6$ in t-amylalcohol is added a 10 ml toluene solution of 30 g (0.5 eq.) methylcyclosiloxane (C1H$_4$OSi)$_n$, (from Huls Petrarch Silicon Co., Catalog No. M 8830, n=4–8), at 65°–70° C. for 30 min. The mixture is then reacted at 70°–75° C. for another 8 hrs. To the solution is added 0.06 g of 5% $H_2PtCl_6$ in t-amyl alcohol and 10.42 g of styrene (0.1 mole). The mixture is reacted at 75°–80° C. for 2 hrs. The mixture is then dissolved in 150 ml methylethylketone and the solution is washed succesively four times with 50 ml portions of $H_2O$. The organic layer is collected and 95 g. of a viscous, straw color product is obtained after stripping off the solvent and excessive styrene at <120° C./<15 mm Hg. The structure is confirmed by IR.

IR (neat): 3450–3500 cm−1 (broad, aromatic hydroxyl), 1100 cm−1 (strong, siloxane), Si—H bond absorption peak at 2150 cm−1 disappears.

EXAMPLE 6

Preparation of Aromatic Hydroxyl-Containing Compound with Organosiloxane Moiety

To a 60 ml toluene solution containing 100 g of trimethylsiloxy terminated methylhydrosiloxanedimethylsiloxane copolymer (MW=2250, methylhydrosiloxane=18% of total copolymer) and 51 g of 2-methoxy-4-allylphenol (0.3 eq.) is added 0.25 g of 5% H2PtCl6 in t-amyl alcohol at 60° C. The reaction mixture is heated to 70° C. and kept at this temperature for a total of 16 hrs. After dissolving in 500 ml methylethylketone, the solution is washed successively four times with 50 ml H$_2$O. The organic layer is collected and 144 g of a viscous, straw color product is obtained. IR spectra shows strong aromatic hydroxyl absorption peaks at 3450–3500 cm−1 and the Si—H band disappears in IR.

EXAMPLE 7

(A) Preparation of 1,3-bis-(5-vinylnorbornyl)-1,1,3,3-tetramethyldisiloxane

To a 10 ml toluene solution of 60.1 g (0.5 mole) of 5-vinyl-2-norbornene and 0.30 g of 5% $H_2PtCl_6$ in t-amyl alcohol is added 29.6 g of 1,1,3,3-tetramethyldisiloxane (0.22 mole, 90% purity) at 45°–50° C. for 1 hour and 30 minutes. The reaction is complete after keeping the reaction at 55°–60° C. for 6 hours. The mixture is then dissolved in 250 ml methyl ethyl ketone. After washing successively with 100 ml portions of water four times, 65 g of 1,3-bis(5-vinylnorbornyl)-1,1,3,3-tetramethyldisiloxane is obtained after stripping off solvent at 120° C./110 mm Hg. The structure of the product is confirmed by IR and 1H NMR as follows:

IR (neat): 1050–1150 cm$^{-1}$ (strong, siloxane), ≡Si—H bond absorption peak at 2150 cm$^{-1}$ disappeared.

1H NMR (CDCl$_3$-TMS): 0–0.7 ppm (m, ≡Si—CH$_3$ and ≡Si—CH$_2$—), 1.0–2.7 ppm (m, aliphatic and cycloaliphatic C—H), 4.85–5.2 ppm (m, alkene C—H) and 5.5–6.2 ppm (m, alkene C—H).

(B) Preparation of 1,3-bis(5-(2,4-dihydroxyl phenyl ethyl)norbornyl)-1,1,3,3-tetramethyl disiloxane To a 80 ml chlorobenzene solution of 22 g (0.2 mole) resorcinol, and 0.38 g methylsulfonic acid is added a 15 ml chlorobenzene solution of 37.4 g (0.1 mole) of the 1,3-bis(5-vinylnorbornyl)-1,1,3,3-tetramethyldisiloxane prepared in (A) above at 100° C. in 25 minutes. The mixture is reacted at 100° C. to 105° C. for 3 hours. After hydrolysis, the solution is washed successively three times with 100 ml portions of water. A viscous semi-solid (54 g) having a brown color is obtained after stripping off solvent at 140° C. and <10 mm Hg. The structure of the product, 1,3-bis(5-(2,4-dihydroxyl phenyl ethyl)norbornyl)-1,1,3,3-tetramethyl disiloxane, is confirmed by IR (neat) and 1H NMR:

IR (neat): 3400 (broad, aromatic hydroxyl), 1050 (strong, siloxane) cm$^{-1}$;

1H NMR (CDCl$_3$): 0–0.7 ppm (m, Si—CH$_3$ and Si—CH=), 1.0–3.0 ppm (m, cycloaliphatic C—H), 5.8–6.0 ppm (D$_2$O exchangeable), 6.5–7.3 ppm (m, Ar—H).

EXAMPLE 8

Preparation of 1,3-bis-((2-cyclohexenyl)-ethyl)-1,1,3,3-tetramethyldisiloxane

To a 20 ml toluene solution of 51.93 g (0.48 mole) of 4-vinylcyclohexene-1 and 0.37 g of 5% $H_2PtCl_6$ in t-amyl alcohol is added 33.6 (0.23 mole, 90% purity) of 1,1,3,3-tetramethyldisiloxane at 45° C. to 50° C. for 1 hour and 30 minutes. The reaction is complete after maintaining the reaction at 55° C. for 5 hours. To this mixture is added 250 ml methyl ethyl ketone. After washing successively with four 100 ml portions of H$_2$O, 78 g (>95% purity by GC) of 1,3-bis-((2-cyclohexenyl)-ethyl)-1,1,3,3-tetramethyldisiloxane having a light yellowish color is obtained after stripping off solvent at 120° C. and <10 mm Hg. The structure of the product, 1,3-bis-((2-cyclohexenyl)ethyl-1,1,3,3-tetramethyldisiloxane, is confirmed by IR and 1H NMR as follows:

IR (neat): 1050–1150 cm$^{-1}$ (strong, siloxane); ≡Si—H bond absorption peak at 2150 cm$^{-1}$ disappeared;

1H NMR (CDCl$_3$): 0.5–0.7 ppm (m, Si—CH$_3$ and Si—CH$_2$—), 1.0–2.2 ppm (m, aliphatic and cycloaliphatic C—H), 5.8 ppm (s, alkene C—H).

EXAMPLE 9

Preparation of 1,3-bis-(2-(4-vinylphenyl)-ethyl)-1,1,3,-tetra-methyl-disiloxane

To a 15 ml toluene solution of 26 g (0.2 mole) 1,4-divinylbenzene and 0.15 g of 5% H$_2$PtCl$_6$ in t-amyl alcohol, is added 14.89 g (90% purity) 1,1,3,3-tetramethyldisiloxane at 35°–40° C. for 15 minutes, then reacted at 45° C. to 50° C. for 6 hours. The solution is washed successively with three 15 ml portions of H$_2$O. 27 g of a light color 2:1 molar liquid adduct, 1,3-bis-(2-(4-vinyl-phenyl)-ethyl)-1,1,3,-tetramethyldisiloxane, is obtained.

EXAMPLE 10

Epoxidation of 1,3-bis-(3-(2-hydroxylphenyl)-propyl)-1,1,3,3-tetramethyldisiloxane Into a 1-liter reaction vessel equipped with temperature and pressure control and indicating means, is added 80.4 (0.4 eq) of 1,3-bis-(3-(2-hydroxylphenyl)-propyl)-1,1,3,3-tetramethyldisiloxane, 298 g (3.2 mole) of epichlorohydrin and 128 g of 1-methoxy-2-hydroxy propane. Equipment used for condensing, separating water from a co-distillate mixture of water, solvent and epichlorohydrin and for returning the solvent and epichlorohydrin to the reaction vessel is installed. After stirring at room temperature at atmospheric pressure to thoroughly mix the contents, the temperature is raised to about 50° C. and the pressure is reduced in order to provide the codistillate with a boiling point at 50° C. To the resultant solution is continuously added a 50% aqueous sodium hydroxide solution 32.6 g (0.42 eq.) over 4.5 hrs. During the addition of the sodium hydroxide aqueous solution, the water is removed by co-distilling with epichlorohydrin and solvent. The distillate is condensed thereby forming two distinct phases, an aqueous phase (top) and an organic epichlorohydrin-solvent phase (bottom). The bottom layer is continuously returned to the reaction vessel. After finishing addition of sodium hydroxide aqueous solution, the mixture is digested at the boiling point for 1.5 hr. The salt is removed by filtration and the mixture is dissolved into 150 ml methyl ethyl ketone and washed successively with water to remove remaining salt and subsequently distilled at 5 mm Hg/100°–120° C. to give 101 g of epoxidized product with epoxide content 15.1% (theoretical epoxide content 16.73%).

EXAMPLE 11

(A) Preparation of 1,3-bis[3'-(4-hydroxyl-2-methoxyphenyl)-propyl]-1,1,3,3-tetramethyldisiloxane To a 40 ml toluene solution of 82.1 g 2-methoxy-4-allylphenol (0.5 mole) and 0.30 g 5% H2PtCl6 in t-amyl alcohol is added a 40 ml toluene solution of 36.76 (0.26 mole) 95% 1,1,3,3-tetramethyldisiloxane at 60° C. The addition is complete in 3 hr3. The mixture is then heated at 60°–65° C. for 3 hr untill IR spectra shows no Si—H absorption at 2160 cm−1. The mixture is dissolved in 250 ml methylethylketone, after washing with H2O (100 ml×3) successively, 115 g of 2:1 adduct 1,3-bis-[3'-(4-hydroxyl-2-methoxyphenyl)-propyl]-1,1,3,3-tetramethyldisiloxane with yellow color is obtained after stripping off solvent at 100 deg. c./<5 mmHg. The structure is confirmed by 1H NMR and IR.

IR(neat): 3350 (broad, aromatic hydroxyl), 1050–1100 (strong, siloxane) cm−1;

1H NMR (CDCl$_3$-TMS): 0–0.8 ppm, (m, Si—CH3 & Si—CH2—), 1.6 ppm (m, —CH2—), 2.7 ppm (t, —CH2—), 5.5–5.6 ppm (broad, D2O exchangable), 6.8–7.0 ppm (m, Ar—H).

(B) Epoxidation of 1,3-bis-[3'-(4-hydroxyl-2-methoxyphenyl)-propyl]-1,1,3,3-tetramethyldisiloxane To a 1-liter reaction vessel equipped with temperature and pressure control and indicating means, is added 79.7 g (0.35 eq.) 1,3-bis-[3'-(4-hydroxyl-2-methoxyphenyl)-propyl]-1,1,3,3-tetramethyldisiloxane from A, 298 g (3.2 mole) of epichlorohydrin and 128 g of 1-methoxy-2-hydroxy propane. Equipment used for condensing, separating water from a co-distillate mixture of water, solvent and epichlorohydrin and for returning the solvent and epichlorohydrin to the reaction vessel is installed. After stirring at room temperature at atmospheric pressure to thoroughly mix the contents, the temperature is raised to about 50°–52° C. and the pressure is reduced in order to provide the co-distillate with a boiling point at 52° C. To the resultant solution is continuously added a 50% aqueous sodium hydroxide solution 35.2 g (0.44 eq.) over 4 hrs and 30 min peiod. During the addition of sodium hydroxide aqueous solution, the water is removed by co-distilling with epichlorohydrin and solvent. The distillate is condensed thereby forming two distinct phases, an aqueous phase (top) and an organic epichlorohydrin-solvent phase (bottom). The bottom layer is continueously returned to the reaction vessel. After finishing addition of sodium hydroxide aqueous solution, the mixture is digested at the boiling point for 1 hr. The salt is removed by filtration and the mixture is dissolved into 150 ml methylethylketone and washed successively with water to remove remaining salt and subsequently distilled at 5 mm Hg/120° C. to give 105 g of epoxidized product with an epoxide content of 14.88% (theoretical epoxide content=18.59%).

EXAMPLE 12

Preparation of an advanced epoxy resin from 1,3-bis(3-(2-hydroxylphenyl)-propy)-1,1,3,3-tetramethyldisiloxane and o-cresolformaldehyde epoxy novolac resin.

0.12 g of ethyltriphenylphosphonium acetate.acetic acid complex catalyst is added to a mixture containing 30.15 g of 1,3-bis(3-2-hydroxylphenyl)-propyl)-1,1,3,3-tetramethyldisiloxane prepared in Example I and 191 g of an o-cresol-formaldehyde epoxy novolac resin having a viscosity at 150° C. of 250 cks (250×10$^{-3}$ m$^2$/s), an average functionality of 5.5 and an epoxide equivalent weight (EEW) of 191. After 2 hours at 140° C. followed by 4 hours at 180° C., the reactant is poured into an aluminum dish and the product has viscosity at 150° C. of 662 cks (662×10$^{-3}$ m$^2$/s) and an EEW of 222.

EXAMPLE 13

Preparation of an advanced epoxy resin from 1,3-bis(3-(2-hydroxyphenyl)-propyl)-1,1,3,3,-tetramethyldisiloxane and 1,1,1-tris-(4-hydroxylphenyl)-methine epoxide 0.5 g of ethyltriphenylphosphonium acetate.acettic acid complex catalyst is added at 80°-90° C. to a mixture containing 30 g of 1,3-bis(3-(2-hydroxylphenyl)-propyl)-1,1,3,3-tetramethyl-disiloxane (Example 1) and 200 g of an triglycidylethers of 1,1,1-tris(4-hydroxylphenyl)-methine having a viscosity at 150° C. of 36 cks ($36 \times 10^{-6}$ m²/s) and an epoxide equivalent weight (EEW) 159.3 (epoxide content 27%). After at 160° C./2 hrs. and 180° C./2 hrs., 210 g of advanced resin with an epoxide content of 20.95% (EEW 205.3) and a viscosity at 150° C. of 73 cks ($73 \times 10^{-6}$ m²/s) is obtained.

EXAMPLE 14

The properties of the individual chemical structures and composition of the Resin formulations by in situ blending siloxane oligomer (Examples 1-4) containing aromatic hydroxyl reactive groups with epoxides and curing agents are provided in Table 1. TEN exposide is triglycidyl ethers of 1,1,1-tris-(4-hydroxyphenyl)-methine having an epoxide content of 27% (EEW=159.3) and CEN epoxide is a 5.5 functional cresol epoxy novolac having an epoxide content of 22.5 percent (EEW=191). ERL-4221 is a cycloaliphatic epoxide (3,4-epoxycyclohexylmethyl-3',4'-epoxycyclohexane carboxylate) available from Union Carbide Co with epoxide 31% (EEW=138). All the curing agents and catalysts employed are commercially available. DADS is 4,4'-diaminodiphenyl sulphone, HHPA is hexahydrophthalic anhydride and HJR 2210 is a phenol-formaldhyde novolac resin (equivalent weight=104; average functionality =5). A-1 catalyst is ethyltriphenylphosphonium acetate.acetic acid complex;. Ph₃P catalyst is triphenylphosphine, and 2E4MI catalyst is 2-ethyl-4-methylimidazole. These catalyst are used for promoting cure for the epoxy resins. The aromatic hydroxyl containing compounds with organosiloxane moieties are different in their aromatic hydroxy content per molecule, their chain length and molecular structure (such as side chain) and are listed in Table 1.

Casting preparation and tests: Castings are made by heating the epoxides, siloxane oligomers and the curing agents at 80°-90° C. to facilitate mixing. A mixing ratio of 0.95 to 1.0 equivalent of curing agent to one equivalent of epoxide will result in the desired properties. The catalyst should be added just prior to use, at the lowest possible temperature, to ensure the longest usable life. The mixture is then degassed at <120° C. under vacuum (<15 mmHg) to remove entrapped air and poured into a pre-heated mold (100° C. to 120° C.). The mixture is cured at the condition listed on Table 1. Glass transition temperature is measured by TMA (thermal mechanical analysis) and DSC (differential scanning calorimetry) by using a DuPont 1090 analyzer.

TABLE 1

| EXAMPLES | A* | B | C | D | E | F |
|---|---|---|---|---|---|---|
| Epoxy, type | CEN | CEN | CEN | CEN | CEN | CEN |
| EEW | 191 | 191 | 191 | 191 | 191 | 191 |
| grams | 10 | 10 | 10 | 10 | 10 | 10 |
| Siloxane of Example | — | 3 | 3 | 2 | 4 | 1 |
| No. of Phenolic OH groups/mole | — | 3.4 | 3.4 | 2.2 | 5.0 | 2.0 |
| Molecular Weight | — | 2500 | 2500 | 2500 | 3000 | 400 |
| Grams | — | 1.0 | 1.5 | 1.0 | 1.0 | 1.5 |
| Curing Agent, type | HJR2210 | HJR2210 | HJR2210 | HJR2210 | HJR2210 | HJR2210 |
| Equiv. wt. | 104 | 104 | 104 | 104 | 104 | 104 |
| Grams (0.95 eq./epoxide eq.) | 5.17 | 5.17 | 5.17 | 5.17 | 5.17 | 5.17 |
| Catalyst, type | Ph₃P | Ph₃P | Ph₃P | Ph₃P | Ph₃P | Ph₃P |
| grams | 0.05 | 0.05 | 0.05 | 0.05 | 0.05 | 0.05 |
| Curing condition | A¹ | A¹ | A¹ | A¹ | A¹ | A¹ |
| Tg Temperature | | | | | | |
| °C. (DSC) | 184 | 183 | 179 | 178 | 183 | 153 |
| °C. (TMA) | — | — | — | — | — | — |

*Not an example of the present invention.
¹Curing condition A is 125° C. to 130° C. for 1 hour plus 175° C. to 180° C. for 2 hours plus 200° C. to 210° C. for 2 hours.

| EXAMPLES | G* | H | I | J* | K | L |
|---|---|---|---|---|---|---|
| Epoxy, type | TEN | TEN | TEN | TEN | TEN | TEN |
| EEW | 159.3 | 159.3 | 159.3 | 159.3 | 159.3 | 159.3 |
| grams | 10 | 10 | 10 | 10 | 10 | 10 |
| Siloxane of Example | — | 3 | 3 | — | 3 | 3 |
| No. of Phenolic OH groups/mole | — | 3.4 | 3.4 | — | 3.4 | 3.4 |
| Molecular Weight | — | 2500 | 2500 | — | 2500 | 2500 |
| Grams | — | 0.5 | 1.0 | — | 1.0 | 1.5 |
| Curing Agent, type | DADS | DADS | DADS | HJR2210 | HJR2210 | HJR2210 |
| Equiv. wt. | 62 | 62 | 62 | 104 | 104 | 104 |
| Grams (0.95 eq./epoxide eq.) | 3.70 | 3.70 | 3.70 | 6.20 | 6.20 | 6.20 |
| Catalyst, type | A-1 | A-1 | A-1 | A-1 | A-1 | A-1 |
| grams | 0.075 | 0.075 | 0.075 | 0.08 | 0.08 | 0.08 |
| Curing condition | A¹ | A¹ | A¹ | B² | B² | B² |
| Tg Temperature | | | | | | |
| °C. (DSC) | — | — | — | 218 | 212 | 210 |
| °C. (TMA) | 249 | 242 | 246 | — | — | — |

*Not an example of the present invention.
¹Curing condition A is 175° C. to 180° C. for 2 hours plus 230° C. for 4 hours.
²Curing condition B is 125° C. to 130° C. for 1 hour plus 175° C. to 180° C. for 2 hours plus 225° C. to 230° C. for 3 hours.

| EXAMPLES | M | N | O | P* | Q | R |
|---|---|---|---|---|---|---|
| Epoxy, type | TEN | TEN | TEN | TEN | TEN | TEN |
| EEW | 159.3 | 159.3 | 159.3 | 159.3 | 159.3 | 159.3 |
| grams | 10 | 10 | 10 | 10 | 10 | 10 |

TABLE 1-continued

| Siloxane of Example | 4 | 4 | 1 | — | 4 | 1 |
|---|---|---|---|---|---|---|
| No. of Phenolic OH groups/mole | 5.0 | 5.0 | 2 | — | 5.0 | 2 |
| Molecular Weight | 3000 | 3000 | 3000 | — | 3000 | 400 |
| Grams | 1.0 | 1.5 | 1.0 | — | 1.0 | 1.0 |
| Curing Agent, type | HJR2210 | HJR2210 | HJR2210 | HHPA | HHPA | HHPA |
| Equiv. wt. | 104 | 104 | 104 | 156 | 156 | 156 |
| Grams (0.95 eq./epoxide eq.) | 6.20 | 6.20 | 6.20 | 9.3 | 9.3 | 9.3 |
| Catalyst, type | A-1 | A-1 | A-1 | 2E4MI | 2E4MI | 2E4MI |
| grams | 0.08 | 0.08 | 0.08 | 0.06 | 0.06 | 0.06 |
| Curing condition | $C^1$ | $C^1$ | $C^1$ | $C^1$ | $D^2$ | $D^2$ |
| Tg Temperature | | | | | | |
| °C. (DSC) | 217 | 218 | 191 | 198 | 198 | 184 |
| °C. (TMA) | — | — | — | — | — | — |

*Not an Example of the Present Invention.
[1]Curing condition C is 125° C. to 130° C. for 1 hour plus 175° C. to 180° C. for 2 hours plus 225° C. to 230° C. for 3 hours.
[2]Curing condition D is 130° C. for 1 hour plus 175° C. for 2 hours plus 225° C. for 2 hours.

| EXAMPLES | S* | T | U | V | W | X |
|---|---|---|---|---|---|---|
| Epoxy, type | ERL4221 | ERL4221 | ERL4221 | ERL4221 | ERL4221 | ERL4221 |
| EEW | 138 | 138 | 138 | 138 | 138 | 138 |
| grams | 5 | 5 | 5 | 5 | 5 | 5 |
| Siloxane of Example | — | 3 | 3 | 2 | 1 | 1 |
| No. of Phenolic OH groups/mole | — | 3.4 | 3.4 | 2.2 | 2 | 2 |
| Molecular Weight | — | 2500 | 2500 | 2500 | 400 | 400 |
| Grams | — | 0.25 | 0.5 | 0.5 | 0.5 | 0.75 |
| Curing Agent, type | HHPA | HHPA | HHPA | HHPA | HHPA | HHPA |
| Equiv. wt. | 156 | 156 | 156 | 156 | 156 | 156 |
| Grams (0.95 eq./epoxide eq.) | 10.8 | 10.8 | 10.8 | 10.8 | 10.8 | 10.8 |
| Catalyst, type | 2E4MI | 2E4MI | 2E4MI | 2E4MI | 2E4MI | 2E4MI |
| grams | 0.06 | 0.06 | 0.06 | 0.06 | 0.06 | 0.06 |
| Curing condition | $E^1$ | $E^1$ | $E^1$ | $E^1$ | $E^1$ | $E^1$ |
| Tg Temperature | | | | | | |
| °C. (DSC) | 228 | 216 | 196 | 196 | 198 | 177 |
| °C. (TMA) | — | — | — | — | — | — |

*Not an example of the present invention.
[1]Curing condition E is 130° C. for 1 hour plus 180° C. for 2 hours plus 230° C. for 2 hours.

What is claimed is:

1. An advanced resin prepared by reacting (1) at least one compound containing an average of more than one aromatic hydroxyl group per molecule; and (2) at least one compound containing an average of more then one vicinal epoxy group per molecule; with the proviso that at least one compound of components (2) or (2) is a compound which contains at least one organosiloxane moiety and which compound containing at least one organosiloxane moiety is represented by the following general formulas I or II $$Z-(X''-Ar-(OH)_{n1})_{n2} \quad \text{Formula I}$$

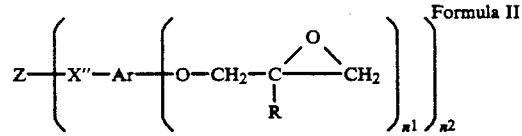

Formula II wherein Ar is any divalent or multivalent aromatic moiety or divalent or multivalent inert substituted aromatic moiety; each R is independently hydrogen or an alkyl group having from 1 to about 3 carbon atoms; each X" is independently a divalent aliphatic or a divalent cycloaliphatic group or a divalent alkoxy or or a divalent cycloalkoxy group having from 2 to about 12 carbon atoms; Z is an $n^2$-valent entity containing at least one organosiloxane moiety; $n^1$ has a value from 1 to about 3; and $n^2$ has a value from 1 to about 200; with the proviso that (a) when $n^2$ has a value of 1, $n^1$ has a value greater than 1; and (b) the group(s)

and/or

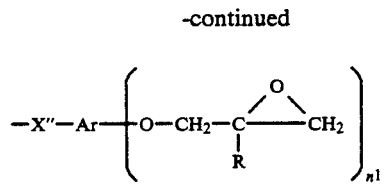

is (are) attached to a silicon atom.

2. An advanced resin of claim 1 wherein
(a) when component (1) contains a compound which contains at least one organosiloxane moiety said compound is represented by the following general formulas X, XI, XII, or XIII

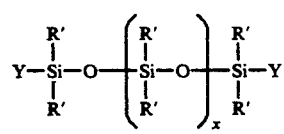

Formula X

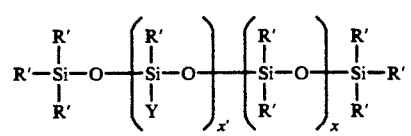

Formula XI

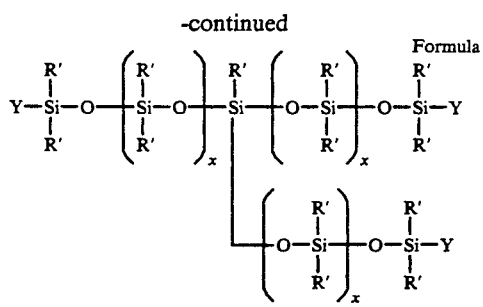

Formula XII

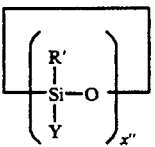

Formula XIII wherein each R' is independently a hydrocarbyl group having from 1 to about 20, carbon atoms; each Y is a hydrocarbyl group having from 2 to about 20 carbon atoms or an entity represented by the following formulas XXII, XXIII, XXIV, XXV, XXVI, XXVII, or XXVIII with the proviso that at least an average of more than one Y is other than a hydrocarbyl group;

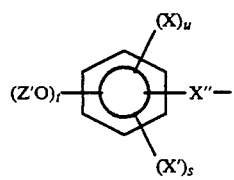

Formula XXII

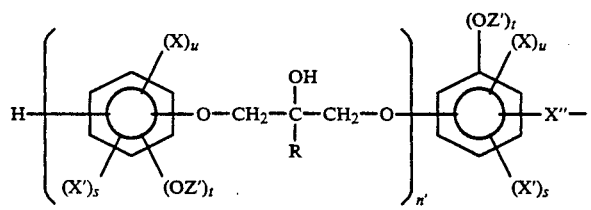

Formula XXIII

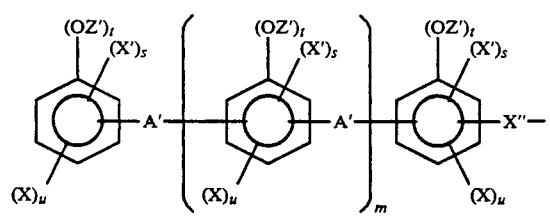

Formula XXIV

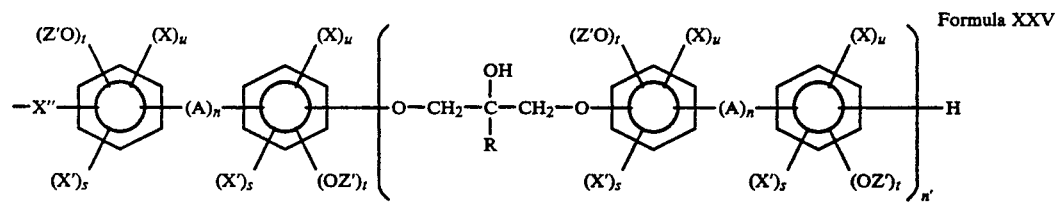

Formula XXV

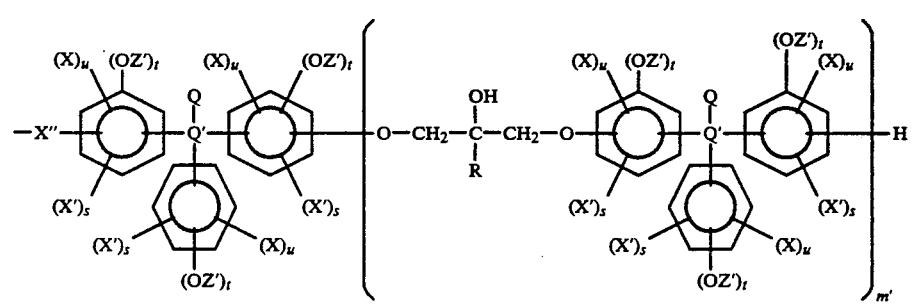

Formula XXVI

-continued

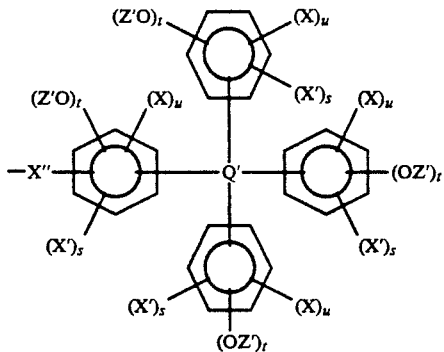

Formula XXVII

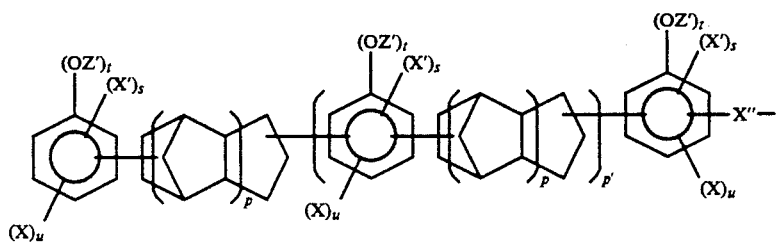

Formula XXVIII wherein each A is independently a divalent hydrocarbyl group having from 1 to about 20 carbon atoms, —O—, —S—, —S—S—, —SO—, —SO$_2$—, or —CO—; each A' is independently a divalent hydrocarbyl group having from 1 to about 20 carbon atoms; each Q is independently hydrogen or an alkyl group having from 1 to about 10 carbon atoms; each Q' is independently a tetravalent hydrocarbyl group having from 1 to about 20 carbon atoms; each R is independently hydrogen or an alkyl group having from 1 to about 3 carbon atoms; each X is independently hydrogen, a hydrocarbyl or hydrocarbyloxy group having from 1 to about 12 carbon atoms, a halogen atom; each X' is independently hydrogen or a monovalent aliphatic or a dmonovalent cycloaliphatic group; each X" is independently a divalent aliphatic or a divalent cycloaliphatic group or a divalent alkoxy or or a divalent cycloalkoxy group having from 2 to about 12 carbon atoms; each Z' is hydrogen; each m independently has an average value from about 0.01 to about 8; each m' independently has an average value from about zero to about 8; each n independently has a value of zero or 1; each n' independently has an average value from about 0.001 to about 20; each $n^1$ independently has a value from 1 to about 3; each p independently has a value from zero to about 10; each p' independently has an average value from zero to about 8; and each s, t and u independently has a value from 1 to about 3 with the proviso that the sum of s, u and t satisfies the valency of the ring; each independently has a value from zero to about 500; each x' independently has a value from 2 to about 500; each x" independently has a value from 3 to about 50; and the sum of x and x' is from about 2 to about 1000; and (b) when component (2) contains a compound which contains at least one organosiloxane moiety said compound is represented by the general Formulas X, XI, XII, or XIII wherein each R' is independently a hydrocarbyl group having from 1 to 20 carbon atoms; each Y is a hydrocarbyl group having from 2 to about 20 carbon atoms or an entity represented by the following formulas XXII, XXIII, XXIV, XXV, XXVI, XXVII, or XXVIII with the proviso that at least an average of more than one Y is other than a hydrocarbyl group:

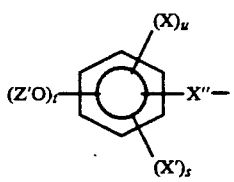

Formula XXII

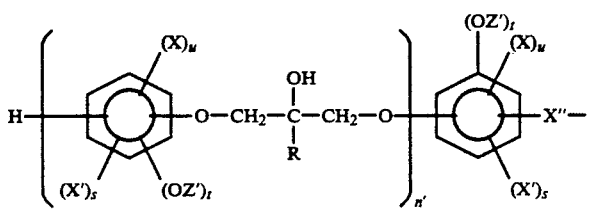

Formula XXIII

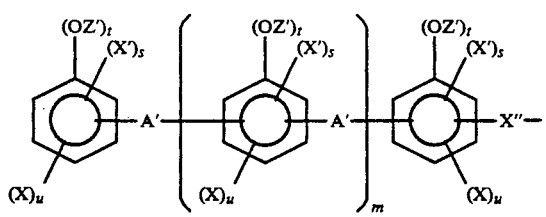

Formula XXIV

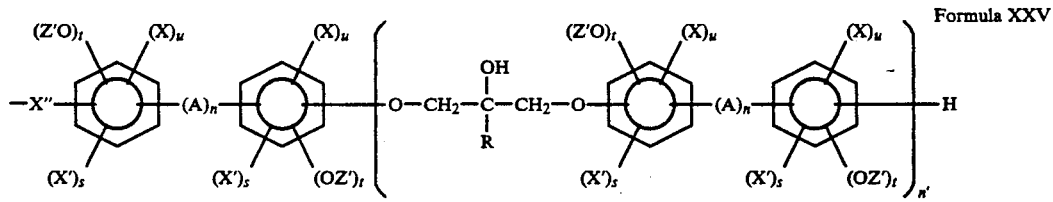

Formula XXV

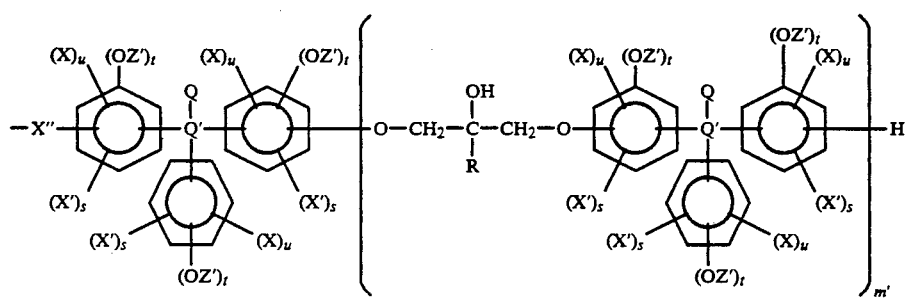

Formula XXVI

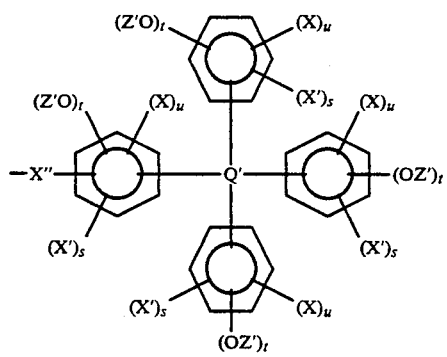

Formula XXVII

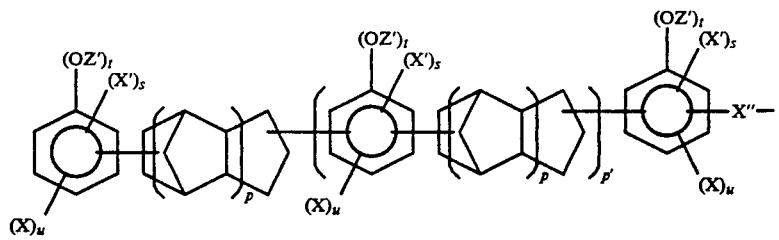

Formula XXVIII wherein each A is independently a divalent hydrocarbyl group having from 1 to about 20 carbon atoms, —O—, —S—, —S—S—, —SO—, —SO₂—, or —CO—; each A' is independently a divalent hydrocarbyl group having from 1 to about 20 carbon atoms; each Q is independently hydrogen or an alkyl group having from 1 to about 10 carbon atoms; each Q' is independently a tetravalent hydrocarbyl group having from 1 to about 20 carbon atoms; each R is independently hydrogen or an alkyl group having from 1 to about 3 carbon atoms; each X is independently hydrogen, a hydrocarbyl or hydrocarbyloxy group having from 1 to about 12 carbon atoms, a halogen atom; each X' is independently hydrogen or a monovalent aliphatic or a monovalent cycloaliphatic group; each X" is independently a divalent aliphatic or a divalent cycloaliphatic group or a divalent alkoxy or or a divalent cycloalkoxy group having from 2 to about 12 carbon atoms; each Z' is independently a glycidyl group; each m independently has an average value from about 0.01 to about 8; each m' independently has an average value from about zero to about 8; each n independently has a value of zero or 1; each n' independently has an average value from about 0.001 to about 20; each $n^1$ independently has a value from 1 to about 3 with the proviso that the sum of s, u and t satisfies the valency of the ring; each p independently has a value from zero to about 10; each p' independently has an average value from zero to about 8; each s, t and u independently has a value from 1 to about 3; each x independently has a value from zero to about 500; each x' independently has a value from 2 to about 500; each x" independently has a value from 3 to about 50; and the sum of x and x' is from about 2 to about 1000.

3. A curable composition comprising (A) at least one compound having an average of more than one vicinal epoxy group and at least one organosiloxane moiety per molecule; and (B) at least one curing agent for component (A), which during agent is free of aromatic hydroxyl groups;

wherein component (A) is an advanced resin which has an average of more than one glycidyl group per molecule prepared by reacting (1) at least one compound containing an average of more than one aromatic hydroxyl group per molecule; and (2) at least one compound containing an average of more than one vicinal epoxy group per molecule; with the proviso that at least one compound of components (1) or (2) is a compound which contains at least one organosiloxane moiety and which compound containing at least one organosiloxane moiety is represented by the following general formulas I or II

   Formula I wherein Ar is any divalent or multivalent aromatic moiety or divalent or multivalent inert substituted aromatic moiety; each R is independently hydrogen or an alkyl group having from 1 to about 3 carbon

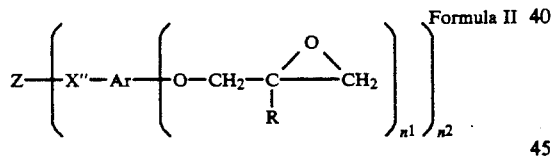   Formula II atoms; each X" is independently a divalent aliphatic or a divalent cycloaliphatic group or a divalent alkoxy or or a divalent cycloalkoxy group having from 2 to about 12 carbon atoms; Z is an $n^2$-valent entity containing at least one organosiloxane moiety; $n^1$ has a value from 1 to about 3; and $n^2$ has a value from 1 to about 200; with the proviso that when $n^2$ has a value of 1, $n^1$ has a value greater than 1.

4. A curable composition of claim 3 wherein
(a) when component (1) contains a compound which contains at least one organosiloxane moiety said compound is represented by the following general formulas X, XI, XII, or XIII

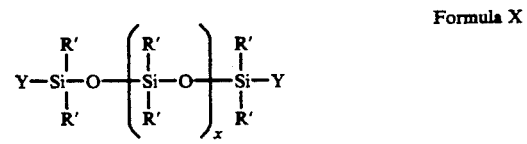   Formula X

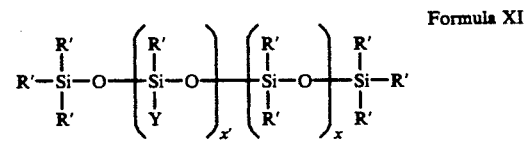   Formula XI

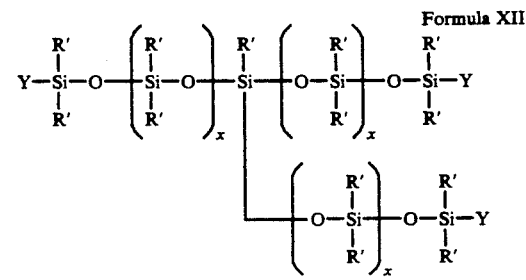   Formula XII

   Formula XIII wherein each R' is independently a hydrocarbyl group having from 1 to about 20, carbon atoms; each Y is a hydrocarbyl group having from 2 to about 20 carbon atoms or an entity represented by the following formulas XXII, XXIII, XXIV, XXV, XXVI, XXVII, or XXVIII with the proviso that at least an average of more than one Y is other than a hydrocarbyl group:

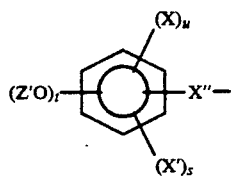   Formula XXII

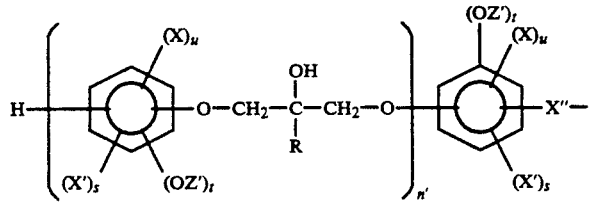   Formula XXIII

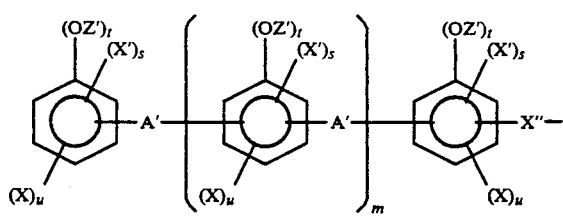 Formula XXIV

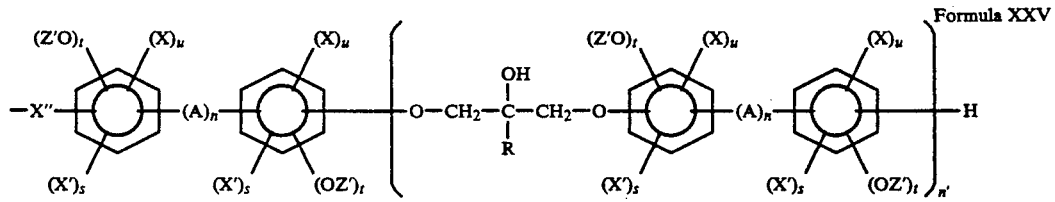 Formula XXV

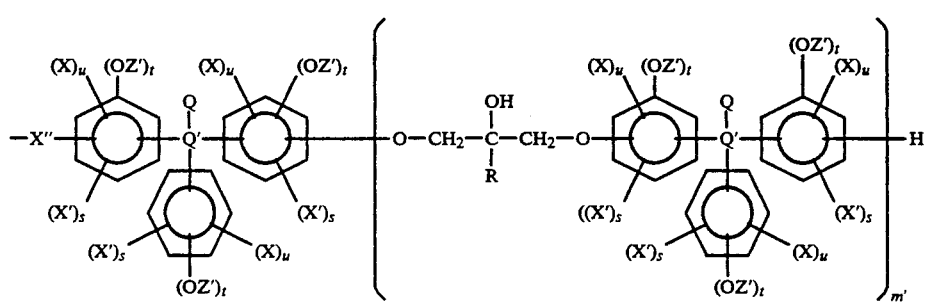 Formula XXVI

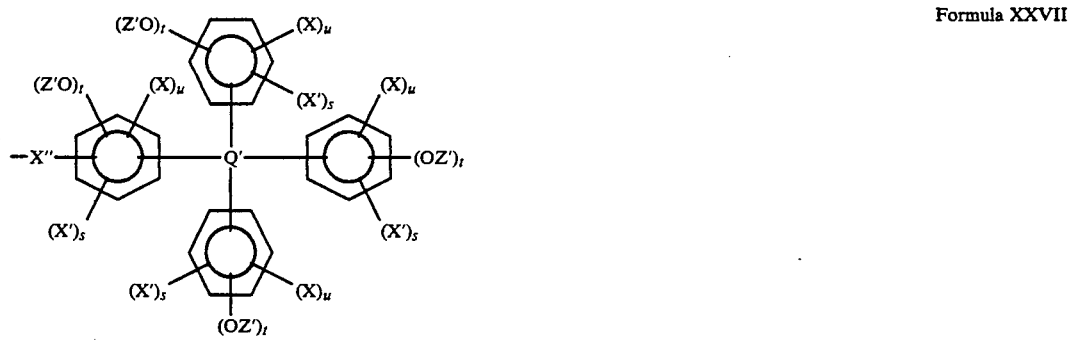 Formula XXVII

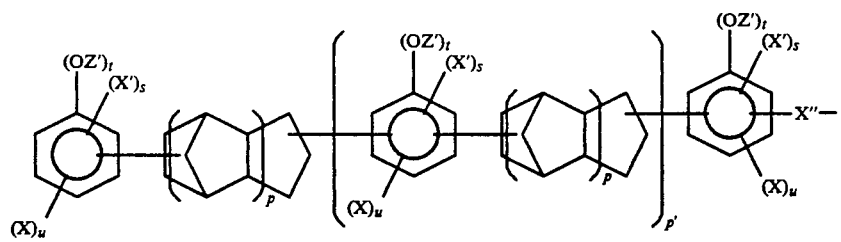 Formula XXVIII wherein each A is independently a divalent hydrocarbyl group having from 1 to about 20 carbon atoms, —O—, —S—, —S—S—, —SO—, —SO$_2$—, or —CO—; each A' is independently a divalent hydrocarbyl group having from 1 to about 20 carbon atoms; each Q is independently hydrogen or an alkyl group having from 1 to about 10 carbon atoms; each Q' is independently a tetravalent hydrocarbyl group having from 1 to about 20 carbon atoms; each R is independently hydrogen or an alkyl group having from 1 to about 3 carbon atoms; each X is independently hydrogen, a hydrocarbyl or hydrocarbyloxy group having from 1 to about 12 carbon atoms, a halogen atom; each X' is independently hydrogen or a monovalent aliphatic or a monovalent cycloaliphatic group; each X'' is independently a divalent aliphatic or a divalent cycloaliphatic group or a divalent alkoxy or or a divalent cycloalkoxy group having from 2 to about 12 carbon atoms; each Z' is hydrogen; each m independently has an average value from about 0.01 to about 8; each m' independently has an average value from about zero to about 8; each n independently has a value of zero or 1; each n' independently has an average value from about 0.001 to about 20; each n$^1$ independently has a value from 1 to about 3; each p independently has a value from zero to about 10; each p' independently has an average value from zero to about 8; and each s, t and u independently has a value from 1 to about 3 with the proviso that the sum of s, u and t satisfies the valency of the ring; each x independently has a value from zero to about 500; each x' independently has a value from 2 to about 500; each x" independently has a value from 3 to about 50; and the sum of x and x' is from about 2 to about 1000; and (b) when component (2) contains a compound which contains at least one organosiloxane moiety said compounds is represented by the general formula X, XI, XII, or XIII wherein each R' is independently a hydrocarbyl group having from 1 to 20 carbon atoms; each Y is a hydrocarbyl group having from 2 to about 20 carbon atoms or an entity represented by the following formulas XXII, XXIII, XXIV, XXV, XXVI, XXVII, or XXVIII with the proviso that at least an average of more than one Y is other than a hydrocarbyl group:

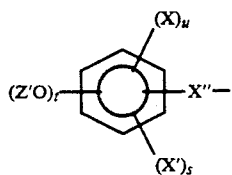

Formula XXII

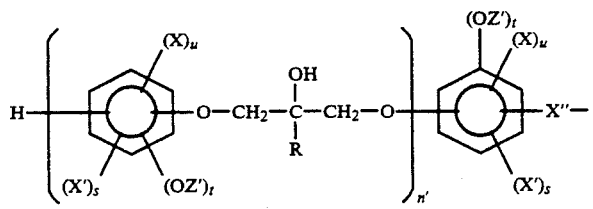

Formula XXIII

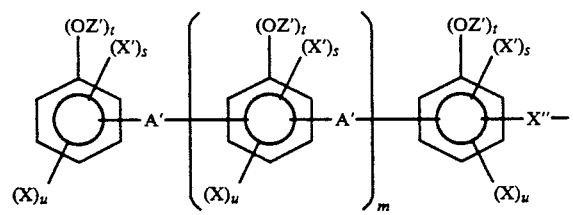

Formula XXIV

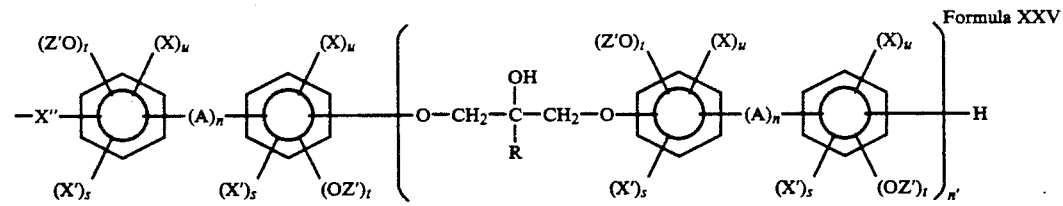

Formula XXV

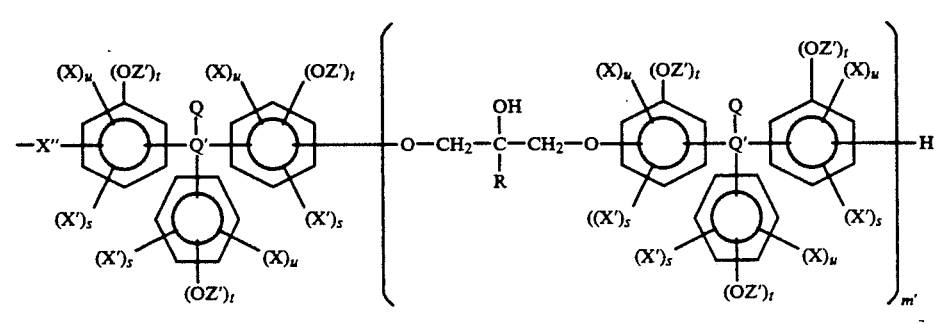

Formula XXVI

Formula XXVII

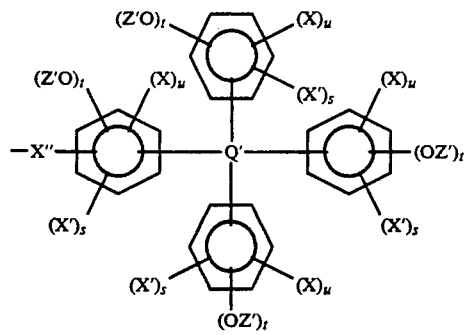

Formula XXVIII

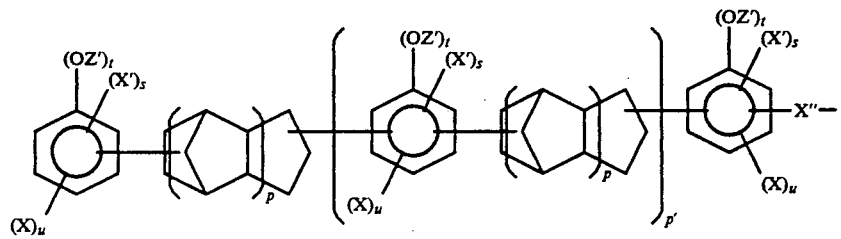

wherein each A is independently a divalent hydrocarbyl group having from 1 to about 20 carbon atoms, —O—, —S—, —S—S—, —SO—, —SO$_2$—, or —CO—; each A' is independently a divalent hydrocarbyl group having from 1 to about 20 carbon atoms; each Q is independently hydrogen or an alkyl group having from 1 to about 10 carbon atoms; each Q' is independently a tetravalent hydrocarbyl group having from 1 to about 20 carbon atoms; each R is independently hydrogen or an alkyl group having from 1 to about 3 carbon atoms; each X is independently hydrogen, a hydrocarbyl or hydrocarbyloxy group having from 1 to about 12 carbon atoms, a halogen atom; each X' is independently hydrogen or a monovalent aliphatic or a monovalent cycloaliphatic group; each X" is independently a divalent aliphatic or a divalent cycloaliphatic group or a divalent alkoxy or or a divalent cycloalkoxy group having from 2 to about 12 carbon atoms; each Z' is independently a glycidyl group; each m independently has an average value from about 0.01 to about 8; each m' independently has an average value from about zero to about 8; each n independently has a value of zero or 1; each n' independently has an average value from about 0.001 to about 20; each n¹ independently has a value from 1 to about 3 with the proviso that the sum of s, u and t satisfies the valency of the ring; each p independently has a value from zero to about 10; each p' independently has an average value from zero to about 8; each s, t and u independently has a value from 1 to about 3; each x independently has a value from zero to about 500; each x' independently has a value from 2 to about 500; each x" independently has a value from 3 to about 50; and the sum of x and x' is from about 2 to about 1000.

5. A curable composition of claim 4 wherein in component (A),
(a) when component (1) contains a compound which contains an organosiloxane moiety, it is
(i) a compound represented by Formula X wherein each R' is a methyl group and x has a value of zero, Y is represented by formula XXII wherein each X is hydrogen or a methoxy group, X' is hydrogen, X" is —CH$_2$—CH$_2$—CH$_2$—, Z" is hydrogen, each s and t has a value of 1; or
(ii) a compound represented by Formula X wherein each R' is a methyl group and x has a value of zero, Y is represented by formula XXII wherein one X is a hydroxyl group and the remaining X groups are hydrogen, X' is hydrogen, X" is the group

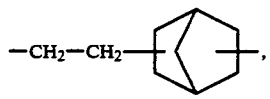

Z is hydrogen, s has a value of 1 and t has a value of 2; or
(iii) a compound represented by Formula XI wherein, each R' is a methyl group, the sum of the average values of x and x' is from about 30 to about 40 with from about 15% to about 85% of the sum being contributed by x and from about 85% to about 15% of the sum being contributed by x', and each Y is a hydrocarbyl group having from about 4 to about 10 carbon atoms or the group represented by formula XXII, wherein each X is hydrogen or a methoxy group, X' is hydrogen, X" is —CH$_2$—CH$_2$—CH$_2$—, each s and t has a value of 1; and, the compound contains an average of from about 2 to about 5 phenolic hydroxyl groups per molecule; or
(iv) a compound represented by Formula XIII wherein R' is a methyl group, X is hydrogen or a methoxy group, X' is hydrogen, X" is a —CH$_2$—CH$_2$—CH$_2$— group, Y is a group represented by Formula XXII, Z' is hydrogen, s has a value of 1, t has a value of 1, and x" has a value from about 4 to about 12;
(b) when component (2) contains a compound which contains an organosiloxane moiety, it is (i) a compound represented by Formula X wherein each R' is a methyl group and x has a value of zero, Y is represented by formula XXII wherein each X is hydrogen or a methoxy group, X' is hydrogen, X" —CH₂—CH₂CH₂—, Z' is a glycidyl group and s has a value of 1; or (ii) a compound represented by Formula X wherein each R' is a methyl group and x has a value of zero, Y is represented by formula XXII wherein each X group is hydrogen or a methoxy group, X' is hydrogen, X" is the group

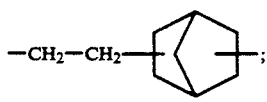

Z' is a glycidyl group, s has a value of 1 and t has a value of 2; or (iii) a compound represented by Formula XI wherein, each R' is a methyl group, the sum of the average values of x and x' is from about 30 to about 40 with from about 15% to about 85% of the sum being contributed by x and from about 85% to about 15% of the sum being contributed by x', and each Y is a hydrocarbyl group having from 4 to about 10 carbon atoms or the group represented by formula III', wherein each X is hydrogen, X¹ is —CH₂—CH₂—CH₂—, Z' is a glycidyl group, and each s and t has a value of 1; or (iv) a compound represented by Formula XIII wherein R' is a methyl group, X is hydrogen or a methoxy group, X' is hydrogen, X" is a —CH₂—CH₂—CH₂— group, Y is a group represented by Formula XXII, Z' i sa glycidyl group, s has a value of 1, t has a value of 1, and x" has a value from about 4 to about 12; and (c) the advanced resin contains an average of from about 2 to about 5 glycidyl ether groups per molecule.

6. A curable composition of claim 3, 4 or 5 wherein component (B) is an aliphatic, cycloaliphatic or aromatic compound containing an average of more than one primary or secondary amine group per molecule, a compound having an average of more than one carboxylic acid group per molecule or an anhydride thereof, a polyamide, a guanidine, or any combination thereof.

7. A curable composition of claim 6 wherein component (B) is 1,2-diaminocyclohexane, bis-(4-aminocyclohexyl)methane, bis-(4-aminophenyl)methane, 4,4'-diaminosulfone, 2-methylimidazole, 2-ethyl-4-methylimidazole, dicyandiamide, hexahydrophthalic anhydride, 5-norbornene-2,3-dicarboxylic anhydride, methyl-5-norbornene-2,3-dicarboxylic anhydride, or any combination thereof.

8. A curable composition comprising (A) at least one compound having an average of more than one vicinal group per molecule and (B) at least one compound having an average of more than one aromatic hydroxyl group per molecule; with the proviso that at least one compound of components (A) and (B) is a compound which contains at least one organosiloxane moiety wherein component (A) contains a compound having an average or more than one vicinal epoxy and at least one organosiloxane moiety per molecule, said compound being represented by the following general formula II

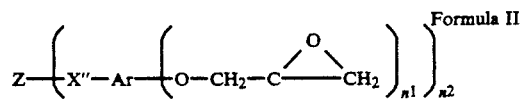

wherein Ar is any divalent or multivalent aromatic moiety or monovalent or multivalent inert substituted aromatic moiety; each R is independently hydrogen or an alkyl group having from 1 to 3 carbon atoms; each X" is independently a divalent aliphatic or a divalent cycloaliphatic group or a divalent alkoxy or a divalent cycloalkoxy group having from 2 to about 12 carbon atoms; Z is an $n^2$-valent entity containing at least one organosiloxane moiety; $n^1$ has a value from 1 to about 3; and $n^2$ has a value from 1 to about 200; with the proviso that (a) when $n^2$ has a value of 1, $n^1$ has a value greater than 1; and (b) the group(s)

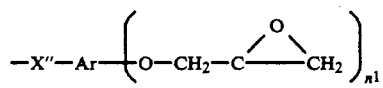

is (are) attached to a silicon atom.

9. A curable composition of claim 8 wherein component (A) contains a compound containing an average of more than one aromatic glycidyl ether group and at least one organosiloxane moiety per molecule, said compound being represented by the following general formulas X, XI, XII, or XIII

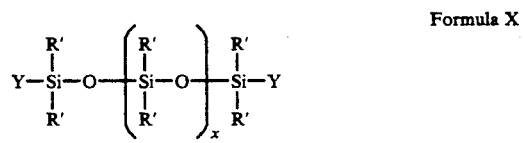

Formula X

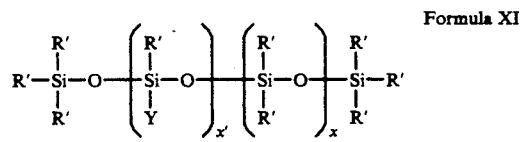

Formula XI

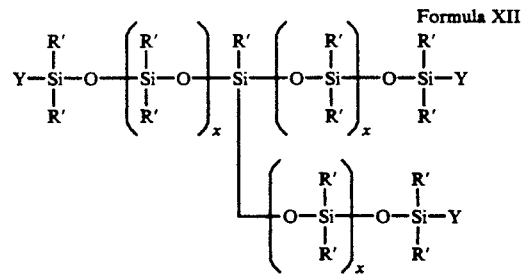

Formula XII

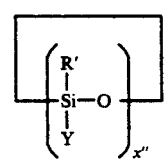

Formula XIII wherein each R' is independently a hydrocarbyl group having from 1 to about 20, carbon atoms; each Y is a hydrocarbyl group having from 2 to about 20 carbon atoms or an entity represented by the following formulas XXII, XXIII, XXIV, XXV, XXVI, XXVII, or XXVIII with the proviso that at least an average of more than one Y is other than a hydrocarbyl group:
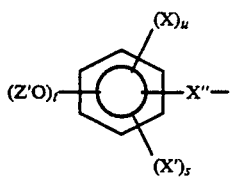
Formula XXII
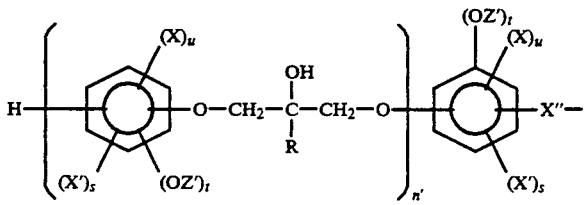
Formula XXIII
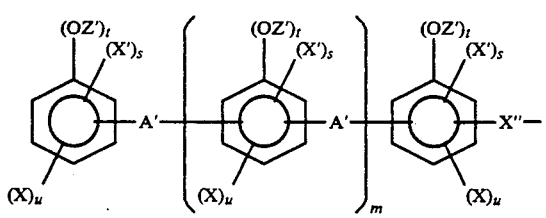
Formula XXIV
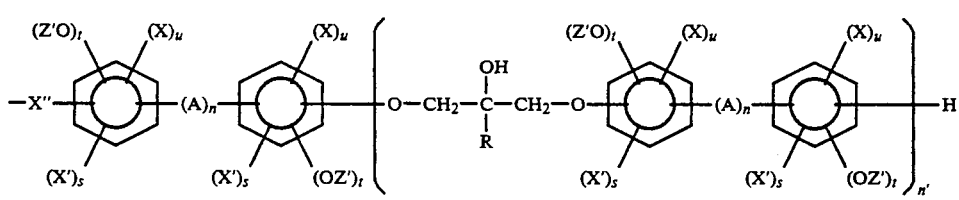
Formula XXV
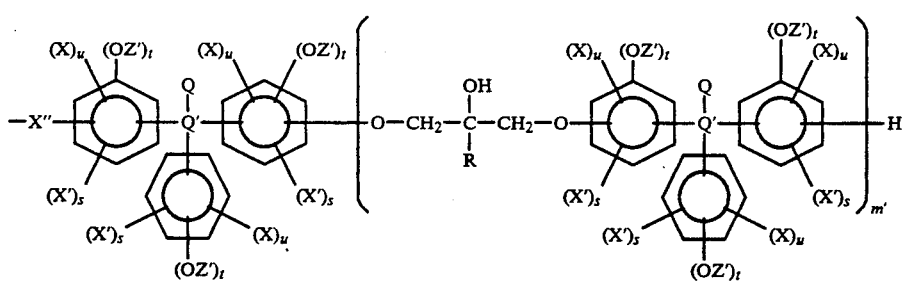
Formula XXVI
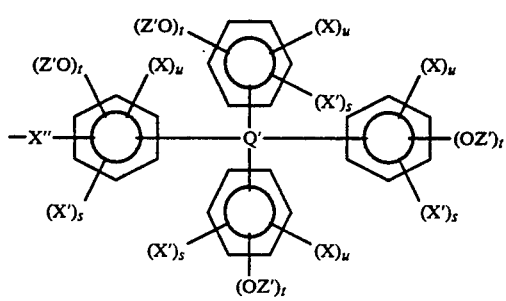
Formula XXVII

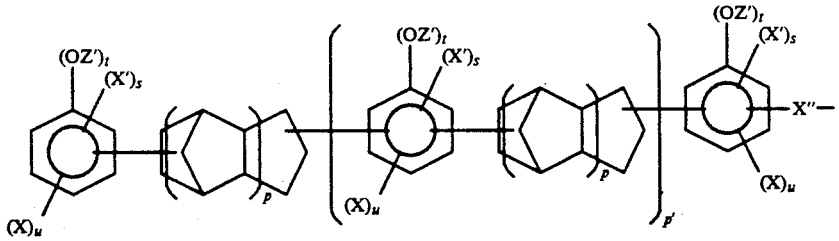

Formula XXVIII wherein each A is independently a divalent hydrocarbyl group having from 1 to about 20 carbon atoms, —O—, —S—, —S—S—, —SO—, or —CO—; each A' is independently a divalent hydrocarbyl group having from 1 to about 20 carbon atoms; each Q is independently hydrogen or an alkyl group having from 1 to about 10 carbon atoms; each Q' is independently a tetravalent hydrocarbyl group having from 1 to about 20 carbon atoms; each R is independently hydrogen or an alkyl group having from 1 to about 3 carbon atoms; each X is independently hydrogen, a hydrocarbyl or hydrocarbyloxy group having from 1 to about 12 carbon atoms, or a halogen atom; each X' is independently hydrogen or a monovalent aliphatic or a monovalent cycloaliphatic group; each X" is independently a divalent aliphatic or a divalent cycloaliphatic group or a divalent alkoxy or or a divalent cycloalkoxy group having from 2 to about 12 carbon atoms; each Z' is independently a glycidyl group with the proviso that at least two of such groups are a glycidyl group; each m independently has an average value from about 0.01 to about 8; each m' independently has an average value from about zero to about 8; each n independently has a value of zero or 1; each n' independently has an average value from about 0.001 to about 20; each $n^1$ independently has a value from 1 to about 3; each p independently has a value from zero to about 10; each p' independently has an average value from zero to about 8; each s, t and u independently has a value from 1 to about 3; each x independently has a value from zero to about 500; each x' independently has a value from 2 to about 500; each x" independently has a value from 3 to about 50; and the sum of x and x' is from about 2 to about 1000.

10. A curable composition of claim 9 wherein in component (A) each R is hydrogen; each R' is independently a hydrocarbyl group having from 1 to about 15 carbon atoms; each A is independently a divalent hydrocarbyl group having from 1 to about 10 carbon atoms, —O—, —S—, —S—S—, —SO—, —SO$_2$—, or —CO—; each A' is independently a divalent hydrocarbyl group having from 1 to about 10, carbon atoms; each Q' is independently a tetravalent hydrocarbyl group having from 1 to about 10 carbon atoms; each X is independently hydrogen, a hydrocarbyl or hydrocarbyloxy group having from 1 to about 6 carbon atoms, or bromine; each X' is independently hydrogen, methyl or methoxy; each X" is independently —CH$_2$—CH$_2$—CH$_2$—, —CH$_2$—CH$_2$—, —O—CH$_2$—CH$_2$—CH$_2$—,

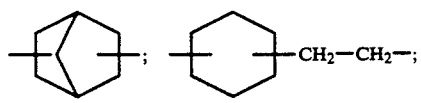

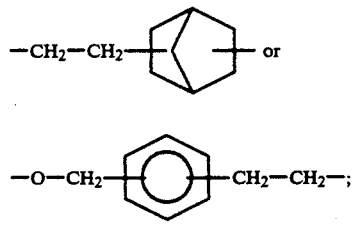

Z' is a glycidyl group; each m independently has an average value from about 1 to about 6; each m' independently has an average value from about 1 to about 6; each n has a value of 1; each n' independently has an average value from about 0.01 to about 12; each $n^1$ independently has a value from 1 to about 3; each p independently has a value from about 1 to about 5; each p' independently has an average value from about 1 to about 6; each s and t independently has a value of 1; each x independently has a value from zero to about 250; each x' independently has a value from 2 to about 250; x" has a value from about 3 to about 40; and the sum of x and x' from about 2 to about 500.

11. A curable composition of claim 10 wherein in component (A) each R' is independently a hydrocarbyl group having from 1 to about 10, carbon atoms; each A is independently a divalent hydrocarbyl group having from 1 to about 10 carbon atoms, —O—, —S—, —S—S—, —SO—, —SO$_2$—, or —CO—; each A' is independently a divalent hydrocarbyl group having from 1 to about 2 carbon atoms; each Q' is independently a tetravalent hydrocarbyl group having from 1 to about 4 carbon atoms; each X is independently hydrogen, a hydrocarbyl or hydrocarbyloxy group having from 1 to about 4 carbon atoms, or bromine; Z' is a glycidyl group; each m independently has an average value from about 2 to about 4; each m' independently has an average value from about about 2 to about 4; each n' independently has an average value from about 0.03 to about 5; each $n^1$ independently has a value of 1; each p independently has a value from about 1 to about 3; each p' independently has an average value from about 2 to about 4; each x independently has a value from zero to about 125; each x' independently has a value from 2 to about 125; x" has a value from about 3 to about 25; and the sum of x and x' is from about 2 to about 250.

12. A curable composition of claim 9 wherein component (A) is selected from the group consisting of
(a) a compound represented by Formula X wherein each R' is a methyl group and x has a value of zero, Y is represented by formula XXII wherein each X is hydrogen or a methoxy group, X' is hydrogen, X" is —CH$_2$—CH$_2$—CH$_2$—, Z' is a glycidyl group, and s and t has a value of 1;

(b) a compound represented by Formula X wherein each R' is a methyl group and x has a value of zero, Y is represented by formula XXII wherein X is hydrogen, X' is hydrogen, X" is the group

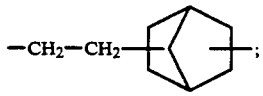

Z' is a glycidyl group; s has a value of 1 and t has a value of 2;

(c) a compound represented by Formula XI wherein, each R' is a methyl group, the sum of the average values of x and x' is from about 30 to about 40 with from about 15% to about 85% of the sum being contributed by x and from about 85% to about 15% of the sum being contributed by x', and each Y is a hydrocarbyl group having from about 4 to about 10 carbon atoms or the group represented by formula III', wherein each X is hydrogen or a methoxy group, X' is hydrogen, X" is —CH$_2$—CH$_2$—CH$_2$—, s has a value of 1; and, the compound contains an average of from about 2 to about 5 glycidyl ether groups per molecule of claim 3, 4, 5 or 6; and (d) a compound represented by Formula XIII wherein R' is a methyl group, X is hydrogen or a methoxy group, X' is hydrogen, X" is a —CH$_2$—CH$_2$—CH$_2$— group, Y is a group represented by Formula XXII, Z' is a glycidyl group, s has a value of 1, t has a value of 1, and x" has a value from about 4 to about 12.

13. A curable composition of claim 8 wherein component (A) contains an advanced resin prepared by reacting (1) at least one compound containing an average of more than one aromatic hydroxyl group per molecule; and (2) at least one compound containing an average of more than one vicinal epoxy group per molecule; with the proviso that at least one compound of components (1) or (2) is a compound which contains at least one organosiloxane moiety and which compound containing at least one organosiloxane moiety is represented by the following general formulas I or II Z—(X"—Ar—(OH)$_{n1}$)$_{n2}$       Formula I

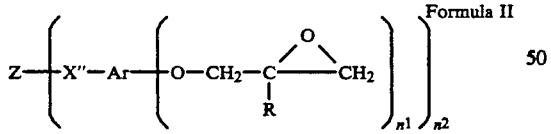     Formula II wherein Ar is any divalent or multivalent aromatic moiety or divalent or multivalent inert substituted aromatic moiety; each R is independently hydrogen or an alkyl group having from 1 to about 3 carbon atoms; each X" is independently a divalent aliphatic or a divalent cycloaliphatic group or a divalent alkoxy or or a divalent cycloalkoxy group having from 2 to about 12 carbon atoms; Z is an n$^2$-valent entity containing at least one organosiloxane moiety; n$^1$ has a value from 1 to about 3; and n$^2$ has a value from 1 to about 200; with the proviso that when n$^2$ has a value of 1, n$^1$ has a value greater than 1.

14. A curable composition of claim 13 wherein in component (A)

(a) when component (1) contains a compound which contains at least one organosiloxane moiety said compound is represented by the following general formulas X, XI, XII, or XIII

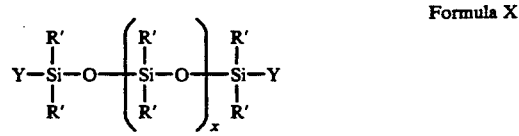

Formula X

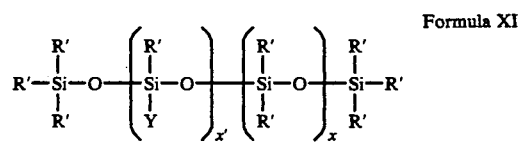

Formula XI

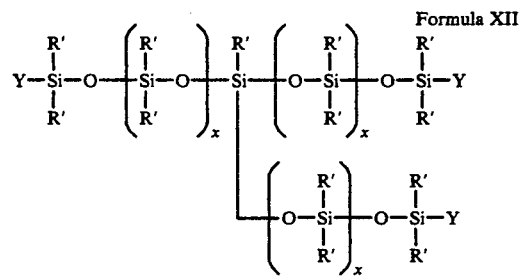

Formula XII

Formula XIII wherein each R' is independently a hydrocarbyl group having from 1 to about 20, carbon atoms; each Y is a hydrocarbyl group having from 2 to about 20 carbon atoms or an entity represented by the following formulas XXII, XXIII, XXIV, XXV, XXVI, XXVII, or XXVIII with the proviso that at least an average of more than one Y is other than a hydrocarbyl group:

Formula XXII

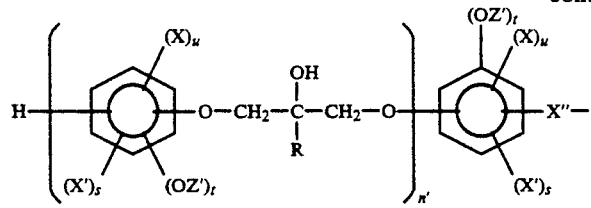

Formula XXIII

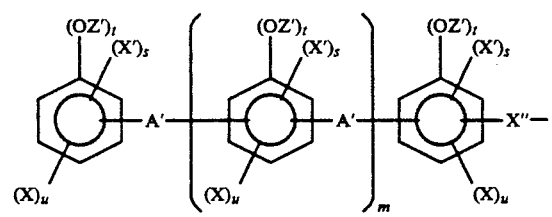

Formula XXIV

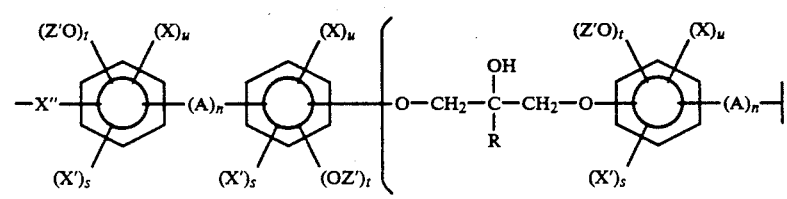

Formula XXV

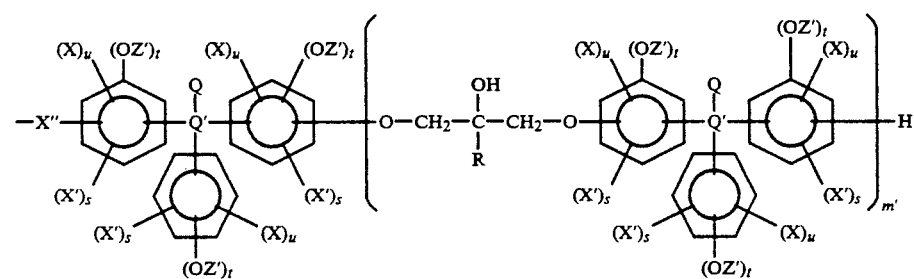

Formula XXVI

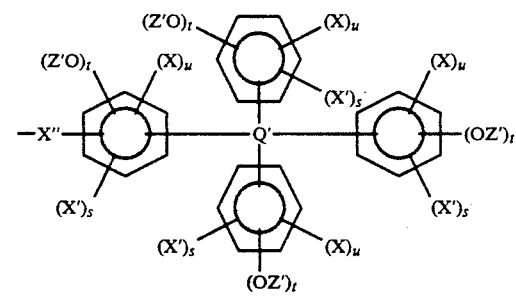

Formula XXVII

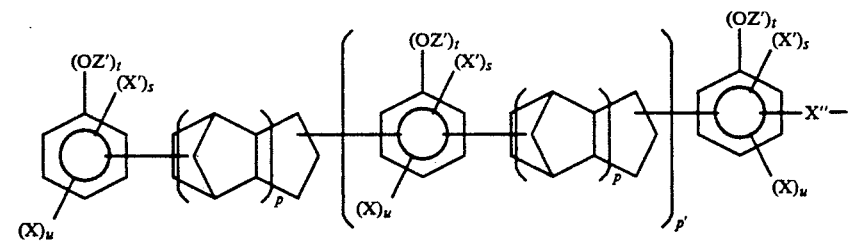

Formula XXVIII wherein each A is independently a divalent hydrocarbyl group having from 1 to about 20 carbon atoms, —O—, —S—, —S—S—, —SO—, —SO$_2$—, or —CO—; each A' is independently a divalent hydrocarbyl group having from 1 to about 20 carbon atoms; each Q is independently hydrogen or an alkyl group having from 1 to about 10 carbon atoms; each Q' is independently a tetravalent hydrocarbyl group having from 1 to about 20 carbon atoms; each R is independently hydrogen or an alkyl group having from 1 to about 3 carbon atoms; each X is independently hydrogen, a hydrocarbyl or hydrocarbyloxy group having from 1 to about 12 carbon atoms, a halogen atom, or a hydroxyl group; each X' is independently hydrogen or a monovalent aliphatic or a monovalent cycloaliphatic group; each X" is independently a divalent aliphatic or a divalent cycloaliphatic group or a divalent alkoxy or or a divalent cycloalkoxy group having from 2 to about 12 carbon atoms; each Z' is hydrogen; each m independently has an average value from about 0.01 to about 8; each m' independently has an average value from about zero to about 8; each n independently has a value of zero or 1; each n' independently has an average value from about 0.001 to about 20; each $n^1$ independently has a value from 1 to about 3; each p independently has a value from zero to about 10; each p' independently has an average value from zero to about 8; and each s, t and u independently has a value from 1 to about 3 with the proviso that the sum of s, u and t satisfies the valency of the ring; each x independently has a value from zero to about 500; each x' independently has a value from 2 to about 500; each x" independently has a value from 3 to about 50; and the sum of x and x' is from about 2 to about 1000; and (b) when component (2) contains a compound which contains at least one organosiloxane moiety said compound is represented by the general Formulas X, XI, XII, or XIII wherein each R' is independently a hydrocarbyl group having suitably from 1 to about 20, more suitably from 1 to about 10, most suitably from 1 to about 4, carbon atoms; each Y is a hydrocarbyl group having from 2 to about 20 carbon atoms or an entity represented by the following formulas XXII, XXIII, XXIV, XXV, XXVI, XXVII, or XXVIII with the proviso that at least an average of more than one Y is other than a hydrocarbyl group:

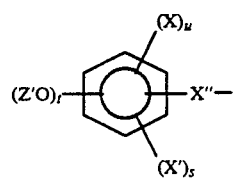

Formula XXII

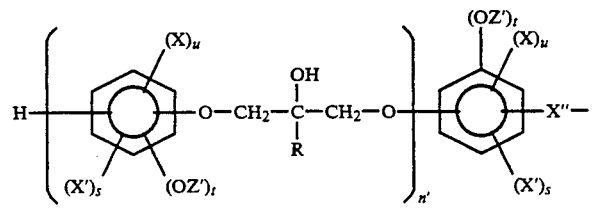

Formula XXIII

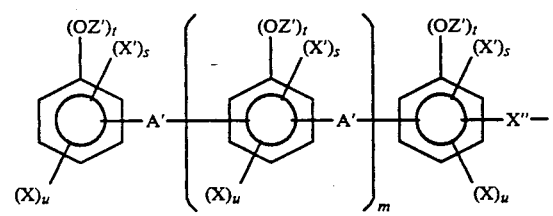

Formula XXIV

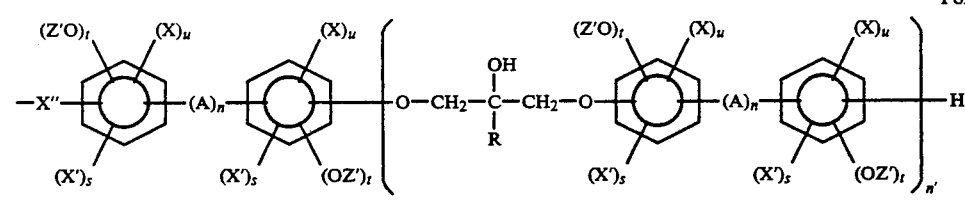

Formula XXV

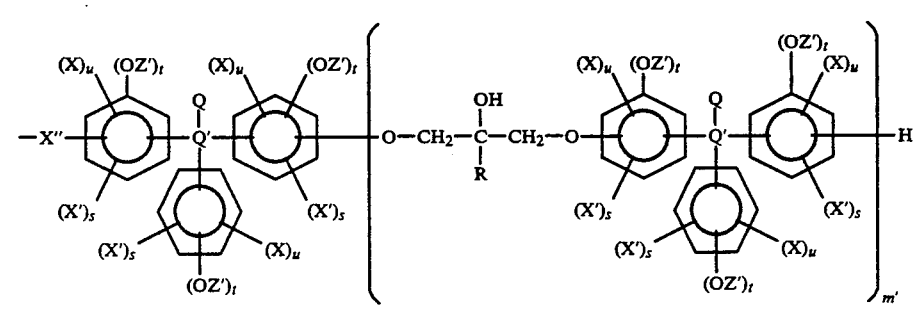

Formula XXVI

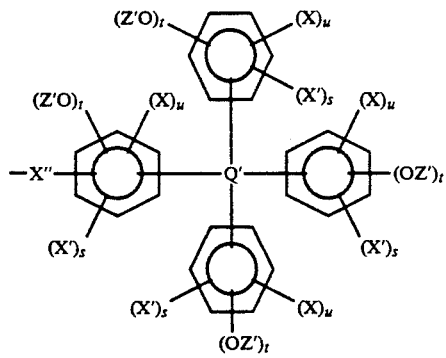

Formula XXVII

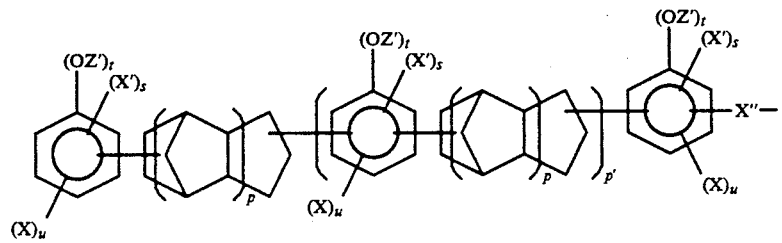

Formula XXVIII wherein each A is independently a divalent hydrocarbyl group having from 1 to about 20 carbon atoms, —O—, —S—, —S—S—, —SO—, —SO$_2$—, or —CO—; each A' is independently a divalent hydrocarbyl group having from 1 to about 20 carbon atoms; each Q is independently hydrogen or an alkyl group having from 1 to about 10 carbon atoms; each Q' is independently a tetravalent hydrocarbyl group having from 1 to about 20 carbon atoms; each R is independently hydrogen or an alkyl group having from 1 to about 3 carbon atoms; each X is independently hydrogen, a hydrocarbyl or hydrocarbyloxy group having from 1 to about 12 carbon atoms, a halogen atom, or an OZ' group; each X' is independently hydrogen or a monovalent aliphatic or a monovalent cycloaliphatic group; each X" is independently a divalent aliphatic or a divalent cycloaliphatic group or a divalent alkoxy or or a divalent cycloalkoxy group having from 2 to about 12 carbon atoms; each Z' is independently a glycidyl group; each m independently has an average value from about 0.01 to about 8; each m' independently has an average value from about zero to about 8; each n independently has a value of zero or 1; each n' independently has an average value from about 0.001 to about 20; each n$^1$ independently has a value from 1 to about 3 with the proviso that the sum of s, u and t satisfies the valency of the ring; each p independently has a value from zero to about 10; each p' independently has an average value from zero to about 8; and each s, t and u independently has a value from 1 to about 3; each x independently has a value from zero to about 500; each x' independently has a value from 2 to about 500; each x" independently has a value from 3 to about 50; and the sum of x and x' is from about 2 to about 1000.

15. A curable composition of claim 14 wherein in component (A) each R is hydrogen; R' is independently a hydrocarbyl group having from 1 to about 15 carbon atoms; each A is independently a divalent hydrocarbyl group having from 1 to about 15 carbon atoms, —O—, —S—, —S—S—, —SO—, —SO$_2$—, or —CO—; each A' is independently a divalent hydrocarbyl group having from 1 to about 10, carbon atoms; each Q' is independently a tetravalent hydrocarbyl group having from 1 to about 10 carbon atoms; each X is independently hydrogen, a hydrocarbyl or hydrocarbyloxy group having from 1 to about 6 carbon atoms, a bromine; each X" is independently hydrogen, —CH$_2$—CH$_2$—CH$_2$—, —CH$_2$—CH$_2$—, —O—CH$_2$—CH$_2$—CH$_2$—,

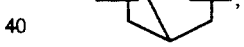

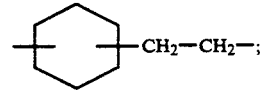

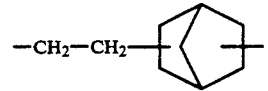

or

each m independently has an average value from about 1 to about 6; each m' independently has an average value from about about 1 to about 6; each n has a value of 1; each n' independently has an average value from about 0.01 to about 12; each n$^1$ independently has a value from 1 to about 3; each p independently has a value from about 1 to about 5; each p' independently has an average value from about 1 to about 6; each s, t and u independently has a value of 1 to 2; each x independently has a value from zero to about 250; each x' independently has a value from 2 to about 250; x" has a value from about 3 to about 40; and the sum of x and x' from about 2 to about 500.

16. A curable composition of claim 15 wherein in component (A) each R' is independently a hydrocarbyl group having from 1 to about 10, carbon atoms; each A is independently a divalent hydrocarbyl group having from 1 to about 4 carbon atoms, —O—, —S—, —S—S—, —SO—, —SO$_2$—, or —CO—; each A' is independently a divalent hydrocarbyl group having from 1 to about 2 carbon atoms; each Q' is independently a tetravalent hydrocarbyl group having from 1 to about 4 carbon atoms; each X is independently hydrogen, a hydrocarbyl or hydrocarbyloxy group having from 1 to about 4 carbon atoms, or bromine; each m independently has an average value from about 2 to about 4; each m' independently has an average value from about about 2 to about 4; each n' independently has an average value from about 0.03 to about 5; each n$^1$ independently has a value of 1; each p independently has a value from about 1 to about 3; each p' independently has an average value from about 2 to about 4; each x independently has a value from zero to about 125; each x' independently has a value from 2 to about 125; x" has a value from about 3 to about 25; and the sum of x and x' is from about 2 to about 250.

17. A curable composition of claim 14 wherein in component (A)

(a) when component (1) contains a compound which contains an organosiloxane moiety, it is (i) a compound represented by Formula X wherein each R' is a methyl group and x has a value of zero, Y is represented by formula XXII wherein each X is hydrogen or a methoxy group, X' is hydrogen, X" is —CH$_2$—CH$_2$—CH$_2$—, Z' is hydrogen, and each s and t has a value of 1; or (ii) a compound represented by Formula X wherein each R' is a methyl group and x has a value of zero, Y is represented by formula XXII wherein one X is a hydroxyl group and the remaining X groups are hydrogen, X' is hydrogen, X" is the group

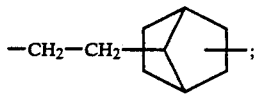

Z' is hydrogen, s has a value of 1 and t has a value of 2; or (iii) a compound represented by Formula XI wherein, each R' is a methyl group, the sum of the average values of x and x' is from about 30 to about 40 with from about 15% to about 85% of the sum being contributed by x and from about 85% to about 15% of the sum being contributed by x', and each Y is a hydrocarbyl group having from about 4 to about 10 carbon atoms or the group represented by formula XXII, wherein each X is hydrogen or a methoxy group, X' is hydrogen, X" is —CH$_2$—CH$_2$—CH$_2$—, each s and t has a value of 1; and the compound contains an average of from about 2 to about 5 phenolic hydroxyl groups per molecule; or (iv) a compound represented by Formula XIII wherein R' is a methyl group, X is hydrogen or a methoxy group, X' is hydrogen, X" is —CH$_2$—CH$_2$—CH$_2$— group, Y is a group represented by Formula XXII, Z' is hydrogen, s has a value of 1, t has a value of 1, and x" has a value from about 4 to about 12; and (b) when component (2) contains a compound which contains an organosiloxane moiety, it is (i) a compound represented by Formula X wherein each R' is a methyl group and x has a value of zero, Y is represented by formula XXII wherein each X is hydrogen, X' is hydrogen, X" is —CH$_2$—CH$_2$—CH$_2$—, Z' is a glycidyl group, and s has a value of 1;

(ii) a compound represented by Formula X wherein each R' is a methyl group and x has a value of zero, Y is represented by formula XXII wherein each X group is hydrogen, X' is hydrogen, X" is the group

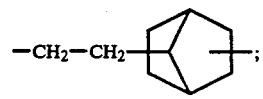

Z' is a glycidyl group, s has a value of 1 and t has a value of 2; or (iii) a compound represented by Formula XI wherein, each R' is a methyl group, the sum of the average values of x and x' is from about 30 to about 40 with from about 15% to about 85% of the sum being contributed by x and from about 85% to about 15% of the sum being contributed by x', and each Y is a hydrocarbyl group having from 4 to about 10 carbon atoms or the group represented by formula III', wherein each X is hydrogen, X' is hydrogen, X" is —CH$_2$—CH$_2$—CH$_2$—, and each s and t has a value of 1; and, the compound contains an average of from about 2 to about 5 glycidyl ether groups per molecule; or (iv) a compound represented by Formula XIII wherein R' is a methyl group, X is hydrogen or a methoxy group, X' is hydrogen, X" is —CH$_2$—CH$_2$—CH$_2$— group, Y is a group represented by Formula XXII, Z' is a glycidyl group, s has a value of 1, t has a value of 1, and x" has a value from about 4 to about 12.

18. A curable composition comprising (A) at least one compound having an average of more than one vicinal epoxy group per molecule and (B) at least one compound having an average of more than one aromatic hydroxyl group per molecule, said compound being represented by the following general formulas X, XI, XII, or XIII

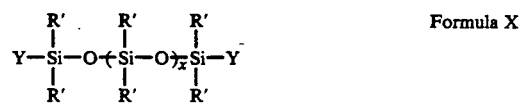

Formula X

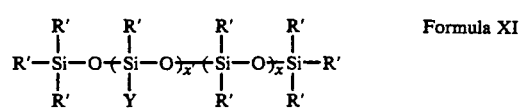

Formula XI

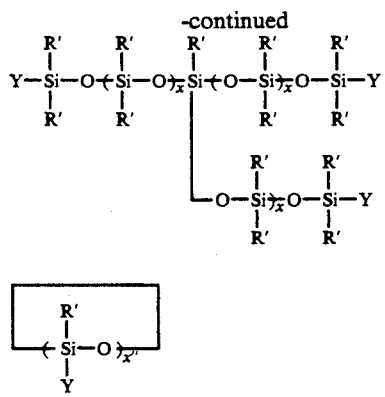
Formula XII

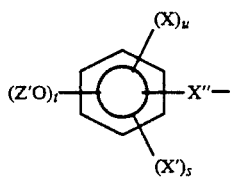
Formula XIII wherein each R' is independently a hydrocarbyl group having from 1 to about 20 carbon atoms; each Y is a hydrocarbyl group having from 2 to about 20 carbon atoms or an entity represented by the following formulas XXII, XXIII, XXIV, XXV, XXVI, XXVII, or XXVIII with the proviso that at least an average of more than one Y is other than a hydrocarbyl group:

about 3 carbon atoms; each X is independently hydrogen, a hydrocarbyl or hydrocarbyloxy group having from 1 to about 12 carbon atoms, a halogen atom, or a hydroxyl group; each X' is independently hydrogen or a monovalent aliphatic or a monovalent cycloaliphatic group; each X" is independently a divalent aliphatic or a divalent cycloaliphatic group or a divalent alkoxy or a divalent cycloalkoxy group having from 2 to about 12 carbon atoms; each Z' is hydrogen; each m independently has an average value from about 0.01 to about 8; each m' independently has an average value from about zero to about 8; each n independently has a value of zero or 1; each n' independently has an average value from about 0.001 to about 20; each $n^1$ independently has a value from 1 to about 3; each p independently has a value from zero to about 10; each p' independently has an average value from zero to about 8; and each s, t and u independently has a value from 1 to about 3 with the proviso that the sum of s, t and u satisfies the valency of the ring; each x independently has a value from zero to about 500; each x' independently has a value from 2 to about 500; each x" independently has a value from 3 to about 50; and the sum of x and x' is from about 2 to

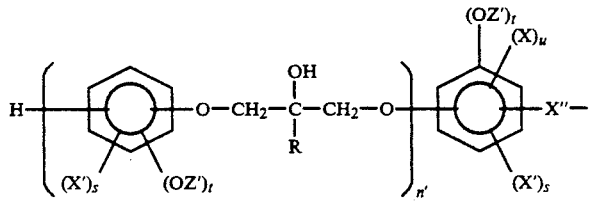
Formula XXII

Formula XXIII

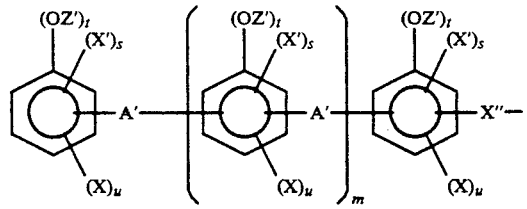
Formula XXIV

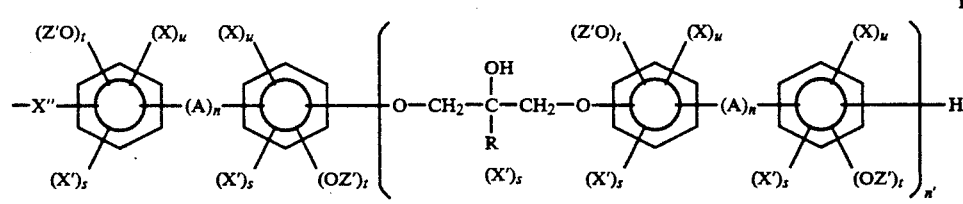
Formula XXV wherein each A is independently a divalent hydrocarbyl group having from 1 to about 20 carbon atoms, —O—, —S—, —S—S—, —SO—, —SO$_2$—, or —CO—; each A' is independently a divalent hydrocarbyl group having from 1 to about 20 carbon atoms; each Q is independently hydrogen or an alkyl group having from 1 to about 10 carbon atoms; each Q' is independently a tetravalent hydrocarbyl group having from 1 to about 20 carbon atoms; each R is independently hydrogen or an alkyl group having from 1 to about 1000.

19. A curable composition of claim 18 wherein in component (B) each R' is independently a hydrocarbyl group having from 1 to about 15 carbon atoms; each A is independently a divalent hydrocarbyl group having from 1 to about 15 carbon atoms, —O—, —S—, —S—S—, —SO—, —SO$_2$—, or —CO—; each A' is independently a divalent hydrocarbyl group having from 1 to about 10, carbon atoms; each Q' is independently a tetravalent hydrocarbyl group having from 1 to about 10 carbon atoms; each R is hydrogen; each X is independently hydrogen, a hydrocarbyl or hydrocarbyloxy group having from 1 to about 6 carbon atoms, or bromine; X' is hydrogen, each X" is independently hydrogen, —CH₂—CH₂—CH₂—, —CH₂—CH₂—, —O—CH₂—CH₂—CH₂—,

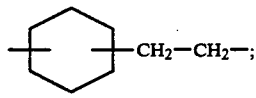

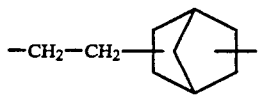

or

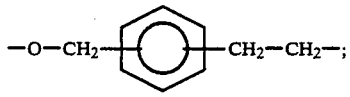

each m independently has an average value from about 1 to about 6; each m' independently has an average value from about 1 to about 6; each n has a value of 1; each n' independently has an average value from about 0.01 to about 12; each n¹ independently has a value from 1 to about 3; each p independently has a value from about 1 to about 5; each p' independently has an average value from about 1 to about 6; each t independently has a value of 1; each x independently has a value from zero to about 250; each x' independently has a value from 2 to about 250; x" has a value from about 3 to about 40; and the sum of x and x' is from about 2 to about 500.

20. A curable composition of claim 19 wherein in component (B) each R' is independently a hydrocarbyl group having from 1 to about 10, carbon atoms; each A is independently a divalent hydrocarbyl group having from 1 to about 10 carbon atoms, —O—, —S—, —S—S—, —SO—, —SO₂—, or —CO—; each A' is independently a divalent hydrocarbyl group having from 1 to about 2 carbon atoms; each Q' is independently a tetravalent hydrocarbyl group having from 1 to about 4 carbon atoms; each X is independently hydrogen, a hydrocarbyl or hydrocarbyloxy group having from 1 to about 4 carbon atoms, or bromine; each m independently has an average value from about 2 to about 4; each m' independently has an average value from about about 2 to about 4; each n' independently has an average value from about 0.03 to about 5; each n¹ has a value of 1; each p independently has a value from about 1 to about 3; each p' independently has an average value from about 2 to about 4; each x independently has a value from zero to about 125; each x' independently has a value from 2 to about 125; x" has a value from about 3 to about 25; and the sum of x and x' is from about 2 to about 250.

21. A curable composition of claim 18 wherein component (B) is selected from the group consisting of
(a) a compound represented by Formula X wherein each R' is a methyl group and x has a value of zero, Y is represented by formula III wherein each X is hydrogen or a methoxy group, X' is hydrogen, X" is —CH₂—CH₂—CH₂—, Z' is hydrogen, and each s and t has a value of 1;
(b) a compound represented by Formula X wherein each R' is a methyl group and x has a value of zero, Y is represented by formula XXII wherein each X group is hydrogen, X' is hydrogen, X" is the group

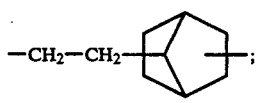

Z' is hydrogen, s has a value of 1, and t has a value of 2;
(c) a compound represented by Formula XI wherein, each R' is a methyl group, the sum of the average values of x and x' is from about 30 to about 40 with from about 15% to about 85% of the sum being contributed by x and from about 85% to about 15% of the sum being contributed by x', and each Y is a hydrocarbyl group having from about 4 to about 10 carbon atoms or the group represented by formula XXII, wherein each X is hydrogen or a methoxy group, X is hydrogen, X" is —CH₂—CH₂—CH₂—, s and t each has a value of 1; and, the compound contains an average of from about 2 to about 5 phenolic hydroxyl groups per molecule; and
(d) a compound represented by Formula XIII wherein R' is a methyl group, X is hydrogen or a methoxy group, X is hydrogen, X" is a —CH₂—CH₂— group, Y is a group represented by Formula XXII, Z' is hydrogen, s has a value of 1, t has a value of 1, and x" has a value from about 4 to about 12.

22. A curable composition of claim 18 wherein at least one compound of component (A) is trisglycidyl ether of 1,1,1-(hydroxyphenyl)methine, o-cresol-formaldehyde epoxy novolac resin, polyglycidyl ether of dicyclopentadiene-phenol resin, diglycidyl ether of bisphenol A, diglycidyl ether of bisphenyl F, diglycidyl ether of 9,9'-bisphenol fluorene, 3,4-epoxycyclohexylmethyl, 3',4'-epoxy cyclohexane carboxylate, or any combinations thereof.

23. An article resulting from curing the curable composition of claim 3, 4, 5, 8, 9, 10, 11, 12, 13, 14, 15, 16, 17, 18, 19, 20, 21 or 22.

24. An article resulting from curing the curable composition of claim 6.

25. An article resulting from curing the curable composition of claim 7.

* * * * *

UNITED STATES PATENT AND TRADEMARK OFFICE
CERTIFICATE OF CORRECTION

PATENT NO.   : 5,206,312
DATED        : April 27, 1993
INVENTOR(S)  : Zeng K. Liao, Chun S. Wang It is certified that error appears in the above-identified patent and that said Letters Patent is hereby corrected as shown below:

In Claim 1, line 37,

"one compound containing an average of more then one"

should read as:

--one compound containing an average of more than one--

In Claim 1, line 39,

"at least one compound of components (2) or (2) is a"

should read as:

--at least one compound of components (1) or (2) is a--

In Claim 2, line 34,

"the valency of the ring; each independently has a "

should read as:

--the valency of the ring; each x independently has a--

UNITED STATES PATENT AND TRADEMARK OFFICE
CERTIFICATE OF CORRECTION

PATENT NO. : 5,206,312  
DATED : April 27, 1993  
INVENTOR(S) : Zeng K. Liao, Chun S. Wang It is certified that error appears in the above-indentified patent and that said Letters Patent is hereby corrected as shown below:

In Claim 4, line 3,

"compounds is represented by the general formula"

should read as :

--compound is represented by the general Formulas--

In Claim 4, line 42,

"iphatic group or a divalent alkoxy or or a divalent"

should read as:

--iphatic group or a divalent alkoxy or a divalent--

In Claim 5, line 30,

"hydrogen, X" is $-CH_2-CH_2-CH_2-$, Z" is"

should read as:

--hydrogen, X" is $-CH_2-CH_2-CH_2-$, Z' is--

UNITED STATES PATENT AND TRADEMARK OFFICE
CERTIFICATE OF CORRECTION

PATENT NO. : 5,206,312

DATED : April 27, 1993

INVENTOR(S) : Zeng K. Liao, Chun S. Wang

It is certified that error appears in the above-identified patent and that said Letters Patent is hereby corrected as shown below:

In Claim 5, line 5,

"hydrogen, X" -$CH_2$-$CH_2CH_2$, Z' is a glyci-"

should read as:

--hydrogen, X" -$CH_2$-$CH_2$-$CH_2$, Z' is a glyci- --

In Claim 5, line 27,

"by Formula XXII, Z' i sa glycidyl group, s has a"

should read as:

--by Formula XXII, Z' is a glycidyl group, s has a--

In Claim 8, line 68,

"an average or more than one vicinal epoxy and at least"

should read as:

--an average or more than one vicinal epoxy about and at least--

UNITED STATES PATENT AND TRADEMARK OFFICE
CERTIFICATE OF CORRECTION

PATENT NO. : 5,206,312

DATED : April 27, 1993

INVENTOR(S) : Zeng K. Liao, Chun S. Wang

It is certified that error appears in the above-indentified patent and that said Letters Patent is hereby corrected as shown below:

In Claim 8, line 12,

"an alkyl group having from 1 to 3 carbon atoms; each"

should read as:

--an alkyl group having from 1 to about 3 carbon atoms; each--

In Claim 9, line 16,

"-O-, -S-, -S-S-, -SO-, or -CO; each A'"

should read as:

-- -O-, -S-, -S-S-, -SO$_2$, or -CO; each A'--

UNITED STATES PATENT AND TRADEMARK OFFICE
CERTIFICATE OF CORRECTION

PATENT NO. : 5,206,312

DATED : April 27, 1993

INVENTOR(S) : Zeng K. Liao, Chun S. Wang

It is certified that error appears in the above-indentified patent and that said Letters Patent is hereby corrected as shown below:

In Claim 14, line 3,

"divalent alkoxy or or a divalent cycloalkoxy group"

should read as:

--divalent alkoxy or a divalent cycloalkoxy group--

Signed and Sealed this

Nineteenth Day of April, 1994

Attest:

BRUCE LEHMAN

*Attesting Officer*  *Commissioner of Patents and Trademarks*